(12) United States Patent
Rao et al.

(10) Patent No.: US 8,518,713 B2
(45) Date of Patent: *Aug. 27, 2013

(54) SELF-ILLUMINATING DOT SYSTEMS AND METHODS OF USE THEREOF

(75) Inventors: Jianghong Rao, Palo Alto, CA (US); Min-kyung So, Palo Alto, CA (US); Chenjie Xu, Mountain View, CA (US); Andreas M. Loening, Stanford, CA (US); Sanjiv S. Gambhir, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/495,208

(22) Filed: Jun. 13, 2012

(65) Prior Publication Data

US 2012/0269734 A1    Oct. 25, 2012

Related U.S. Application Data

(63) Continuation of application No. 12/159,150, filed as application No. PCT/US2007/000096 on Jan. 4, 2007, now Pat. No. 8,263,417.

(60) Provisional application No. 60/756,591, filed on Jan. 4, 2006.

(51) Int. Cl.
*G01N 33/543* (2006.01)

(52) U.S. Cl.
CPC .................................. *G01N 33/543* (2013.01)
USPC ............ 436/518; 436/524; 436/534; 435/7.1; 435/7.92

(58) Field of Classification Search
None
See application file for complete search history.

(56) References Cited

U.S. PATENT DOCUMENTS

| 7,842,469 | B2 * | 11/2010 | Gambhir et al. | 435/7.1 |
| 7,903,061 | B2 | 3/2011 | Zhang et al. | |
| 8,143,013 | B2 | 3/2012 | Ohmiya et al. | |
| 8,216,550 | B2 | 7/2012 | Miller | |
| 8,263,417 | B2 * | 9/2012 | Rao et al. | 436/518 |
| 2002/0155507 | A1 * | 10/2002 | Bruchez et al. | 435/7.2 |
| 2005/0260276 | A1 * | 11/2005 | Yang et al. | 424/492 |
| 2008/0039816 | A1 * | 2/2008 | Svarovsky et al. | 604/503 |
| 2009/0264526 | A1 * | 10/2009 | Sallman et al. | 514/557 |

FOREIGN PATENT DOCUMENTS

| WO | 2004/072232 A | 8/2004 |
| WO | 2005/089409 A2 | 9/2005 |

OTHER PUBLICATIONS

Xu et al., A bioluminescence resonance energy transfer (BRET) system: Application to interacting ciracadian clock proteins, Proc. Natl. Acad. Sci. USA, vol. 96, pp. 151-156, Jan. 1999.*
De Abhijit, et al., "Non-Invasive Imaging of Protein-Protein Interactions from Live Cells and Living Subjects Using Bioluminescence Resonance Energy Transfer" FASEB Journal Express, Oct. 4, 2005, pp. 1-18.
So M-K, et al., "Self-Illuminating Quantum Dot Conjugates for In Vivo Imaging," Nature Biotechnology, Nature Publishing group, vol. 24, No. 3 Mar. 1, 2006.
Supplemental European Search Report, dated Feb. 2, 2010.
Zhang, Yan, et al., "HaloTag protein-mediated site-specific conjugation of bioluminescent proteins to quantum dots," Angewandte Chemie (International Ed. in English) Jul. 24, 2006, vol. 45, No. 30, Jul. 24, 2006, pp. 4936-4940.

* cited by examiner

*Primary Examiner* — Gary W Counts
(74) *Attorney, Agent, or Firm* — Thomas/Horstemeyer, LLP

(57) ABSTRACT

Generally, conjugate systems, self-illuminating quantum dot conjugates, methods of detecting a target in a host, methods of treating a disease in a host, and the like, are described herein.

17 Claims, 22 Drawing Sheets

Scheme 1

Scheme 2

SCHEME 1

SELF-ILLUMINATING DOT SYSTEMS AND METHODS OF USE THEREOF

CROSS-REFERENCE TO RELATED APPLICATION

This application is a continuation of Ser. No. 12/159,150, filed on Jun. 25, 2008, entitled "Self-Illuminating Dot Systems and Methods of Use Thereof", which claims priority to "Self-Illuminating Dot Systems and Methods of Use Thereof", now U.S. Pat. No. 8,263,417, having serial number PCT/US2007/00096, filed on Jan. 4, 2007, which claims priority to the following U.S. provisional application: "Self-Illuminating Dot Systems and Methods of Use Thereof," having Ser. No. 60/756,591, filed on Jan. 4, 2006; which is entirely incorporated herein by reference.

STATEMENT REGARDING FEDERALLY SPONSORED RESEARCH OR DEVELOPMENT

This invention was made with Government support under contract CA114747 awarded by the National Institutes of Health. The Government has certain rights in this invention.

BACKGROUND

Fluorescent semiconductor quantum dots (QDs) have generated wide interest since their initial development and hold exciting potential for molecular imaging in living biological samples. Much of the excitement towards QDs arises from their unique optical properties as fluorescence imaging probes, as compared to traditional organic fluorophores, such as high quantum yield, high molar extinction coefficients, narrow emission spectra, size-dependent tunable emission, and high photostability, all of which make QDs appealing for imaging living subjects. QDs fabricated with various coating molecules and functionalized with biomolecules such as small peptides, proteins, antibodies, and nucleic acids, have been employed in a number of imaging studies. All reported QDs, however, need excitation from external illumination sources in order to fluoresce, which often presents an inherent challenge in imaging opaque subjects such as small living animals. In biological tissues, there are ubiquitous, endogenous chromophores such as collagens, porphyrins, and flavins, which are also excited by the illumination source and lead to significant background autofluorescence. In addition, short-wavelength excitation photons are largely scattered and absorbed in tissues, therefore, little light reaches and excites QDs present at non-superficial locations.

SUMMARY

Generally, aspects of the present disclosure are directed to conjugate systems, self-illuminating quantum dot conjugates, methods of detecting a target in a host, methods of treating a disease in a host, and the like. Embodiments of the present disclosure include a conjugate system, among others, that includes: a self-illuminating quantum dot conjugate system that includes: a self-illuminating quantum dot conjugate and a bioluminescence initiating compound, wherein the self-illuminating quantum dot conjugate includes a bioluminescence donor molecule and a quantum dot, wherein the bioluminescence donor molecule and the bioluminescence initiating compound interact to produce a bioluminescence energy, and wherein the quantum dot emits a fluorescence energy in response to the non-radiative transfer of the bioluminescence energy from the bioluminescence donor molecule to the quantum dot.

Embodiments of the present disclosure include a conjugate system, among others, that includes: a bioluminescence donor molecule and a quantum dot, wherein a bioluminescence energy is produced from the bioluminescence donor molecule, and wherein the quantum dot emits a fluorescence energy in response to the non-radiative transfer of the bioluminescence energy from the bioluminescence donor molecule to the quantum dot.

Embodiments of the present disclosure include, among others, a method of detecting a target in a host that includes: providing a self-illuminating quantum dot conjugate, wherein the self-illuminating quantum dot conjugate includes a bioluminescence donor molecule, a quantum dot, and at least one agent, wherein the agent has an affinity for the target; introducing the self-illuminating quantum dot conjugate to a host; introducing a bioluminescence initiating compound to the host; and determining the presence and location of the target in the host corresponding to the agent by detecting the self-illuminating quantum dot conjugate upon interaction with the bioluminescence initiating compound.

Embodiments of the present disclosure include, among others, treating a disease in a host among others, that includes: providing a self-illuminating quantum dot conjugate, wherein the self-illuminating quantum dot conjugate includes a bioluminescence donor molecule, a quantum dot, and a first agent, wherein the first agent is effective at treating the disease; introducing the self-illuminating quantum dot conjugate to the subject in need for treatment of the disease; introducing a bioluminescence initiating compound to the host; and determining the location of the self-illuminating quantum dot conjugate in the host upon interaction with the bioluminescence initiating compound.

Embodiments of the present disclosure include, among others, a detecting a target in a host that includes: providing a self-illuminating quantum dot conjugate, wherein the self-illuminating quantum dot conjugate includes a bioluminescence donor molecule, a quantum dot, and a first agent, wherein the first agent is disposed between the quantum dot and the bioluminescence donor molecule, and wherein the first agent is degraded by a target; introducing the self-illuminating quantum dot conjugate to a host; introducing a bioluminescence initiating compound to the host; detecting a fluorescent energy emitted from the quantum dot; and determining the presence of the target in the host by detecting the decay of a fluorescent energy emitted from the quantum dot of the self-illuminating quantum dot conjugate upon degradation of the first agent.

Embodiments of the present disclosure include a detecting a target in a system, among others, that includes: providing a bioluminescence donor molecule complex and a quantum dot complex, wherein the bioluminescence donor molecule complex includes a bioluminescence donor molecule, wherein the quantum dot complex includes a quantum dot; introducing each of the bioluminescence donor molecule complex and the quantum dot complex independently to the system, wherein if the system includes the target, the target interacts with at least one of the bioluminescence donor molecule complex or the quantum dot complex to cause the bioluminescence donor molecule complex and the quantum dot complex to become substantially close to one another; introducing a bioluminescence initiating compound to the system, wherein the bioluminescence donor molecule and the bioluminescence initiating compound interact to produce a bioluminescence energy, and wherein the quantum dot emits a fluorescence energy in response to the non-radiative transfer of the bioluminescence energy from the bioluminescence donor molecule to the quantum dot; and determining the presence of the target by detecting the fluorescent energy emitted from the quantum dot.

Embodiments of the present disclosure include a detecting a target in a system, among others, that includes: providing a bioluminescence donor molecule complex and a quantum dot complex, wherein the bioluminescence donor molecule complex includes a bioluminescence donor molecule, wherein the quantum dot complex includes a quantum dot, wherein one of the bioluminescence donor molecule complex or the quantum dot complex includes a first agent that has an affinity for the first target, wherein the first target undergoes a change to a second target upon interaction with the first agent, wherein the other of the bioluminescence donor molecule complex or the quantum dot complex includes a second agent that has an affinity for the second target; introducing each of the bioluminescence donor molecule complex and the quantum dot complex independently to the system, wherein if the system includes the first target the first target undergoes a change to the second target upon interaction with the first agent, wherein the bioluminescence donor molecule complex and the quantum dot complex become substantially close to one another upon interaction of the third agent with the second target; introducing a bioluminescence initiating compound to the system, wherein the bioluminescence donor molecule and the bioluminescence initiating compound interact to produce a bioluminescence energy, and wherein the quantum dot emits a fluorescence energy in response to the non-radiative transfer of the bioluminescence energy from the bioluminescence donor molecule to the quantum dot; and determining the presence of the second target by detecting the fluorescent energy emitted from the quantum dot.

Embodiments of the present disclosure include a detecting a target in a system, among others, that includes: providing a bioluminescence donor molecule complex and a quantum dot complex, wherein the bioluminescence donor molecule complex includes a bioluminescence donor molecule, wherein the quantum dot complex includes a quantum dot, wherein one of the bioluminescence donor molecule complex or the quantum dot complex includes a first agent that has an affinity for the first target, wherein the first agent undergoes a change to a second agent upon interaction with the first target, wherein the other of the bioluminescence donor molecule complex or the quantum dot complex includes a third agent that has an affinity for the second target; introducing each of the bioluminescence donor molecule complex and the quantum dot complex independently to the system, wherein if the system includes the first target the first agent undergoes a change to the second agent upon interaction with the first agent, wherein the bioluminescence donor molecule complex and the quantum dot complex become substantially close to one another upon interaction of the third agent with the second agent; introducing a bioluminescence initiating compound to the system, wherein the bioluminescence donor molecule and the bioluminescence initiating compound interact to produce a bioluminescence energy, and wherein the quantum dot emits a fluorescence energy in response to the non-radiative transfer of the bioluminescence energy from the bioluminescence donor molecule to the quantum dot; and determining the presence of the second target by detecting the fluorescent energy emitted from the quantum dot.

Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3a illustrates that the gel electrophoresis analysis confirmed the size of HTP-Luc8. Both proteins (0.5 µg each) were run on a 4-12% Bis-Tris gradient denaturing gel and stained with Coomassie Blue. The expected sizes for Luc8 and HTP-Luc8 were 37.1 and 70.3 kDa, respectively. FIG. 3b illustrates the bioluminescence emission spectra of Luc8 (solid line) and HTP-Luc8 (dash line). The inset compares the total photon production of Luc8 and HTP-Luc8.

FIG. 5 illustrates a representative bioluminescence emission spectra of the conjugate synthesized at different concentrations of 1 (0, 20, 100, 500, 1000 and 2500 equivalents). FIG. 6 illustrates the total bioluminescence emissions from HTP-Luc8 and from quantum dots, and the calculated BRET ratios of the conjugates prepared in FIG. 5 (in duplicate).

FIG. 8a illustrates a schematic of a QD that is covalently coupled to a BRET donor, Luc8. The bioluminescence energy of Luc8-catalyzed oxidation of coelenterazine is transferred to the QDs, resulting in QD emission. FIG. 8b illustrates the absorption and emission spectra of QD655 ($\lambda$ex=480 nm), and spectrum of the bioluminescent light emitted in the oxidation of coelenterazine catalyzed by Luc8. FIG. 8c illustrates the gel electrophoresis analysis of the conjugation of Luc8 to QD655: (1) unconjugated QD655, (2) the mixture of QD655 and the coupling reagent 1-ethyl-3-(3-dimethylaminopropyl)carbodiimide hydrochloride (EDC), and (3) purified QD655-Luc8 conjugates. FIG. 8d illustrates the bioluminescence emission spectrum of QD655-Luc8 in borate buffer.

FIG. 8e illustrates the bioluminescence emission spectrum of QD655-Luc8 in mouse serum and in whole mouse blood.

FIG. 9a open without filters, and FIG. 9b with 575-650 nm filter. FIG. 9c illustrates the fluorescence imaging of the same mouse injected with indicated solutions in FIG. 9a (excitation filter: 503-555 nm).

FIG. 10a illustrates the overlap of the bioluminescence emission of Luc8 with the absorption spectra of QD605, QD655, QD705, and QD800. FIG. 10b illustrates fluorescence ($\lambda$ex=480 nm), and FIG. 10c illustrates the bioluminescence emission spectra of indicated conjugates. FIG. 10d illustrates the in vitro bioluminescence spectral imaging of solutions containing indicated conjugates. The image was collected for emission from 580 to 850 nm. The different emissions are shown in pseudo colors. The sample at top left contained only Luc8, which showed no detectable long-wavelength (580-850 nm) emission. FIG. 10e illustrates the in vitro bioluminescence spectral imaging of the same samples as in FIG. 10d, but images were collected at the indicated emission wavelength. FIGS. 10f-10i illustrate the multiplex in vivo bioluminescence imaging of the following conjugates subcutaneously injected at indicated sites: (I) QD800-Luc8, 15 pmol; (II) QD705-Luc8, 15 pmol; (III) a mixture of QD655-Luc8, QD705-Luc8, and QD800-Luc8; and (IV) QD655-Luc8, 5 pmol. Images were collected with the following emission filters: FIG. 10f without any filter, FIG. 10g with 575-650 nm filter, FIG. 10h with x-Cy5.5 filter (680-720 nm), and FIG. 10i with ICG filter (810-875 nm). The acquisition time was 2 min.

FIG. 11a illustrates the overlay of fluorescence and differential interference contrast (DIC) images of QD655-Luc8-R9 labeled C6 glioma cells. Fluorescence image was collected with the following filter set (Chroma Technology Corporation, Vermont): excitation, 420/40; emission, D660/40; dichroic, 475DCXR. Scale bar: 50 μm. FIG. 11b illustrates representative bioluminescence images of labeled cells acquired with a filter (575-650 nm) (left) and without any filter (right). FIG. 11c illustrates representative bioluminescence images of a nude mouse injected via tail vein with labeled cells, acquired with a filter (575-650 nm) (left) and without any filter (right). FIG. 11d illustrates a fluorescence image of the same mouse in FIG. 11c (Excitation filter: 503-555 nm). FIG. 11e illustrates an overlay of fluorescence and DIC images of a lung slice of the same mouse imaged in FIG. 11c, and FIG. 11d shows the accumulation of QD conjugates in the lungs; the same filter set as in FIG. 11a was used. Scale bar: 50 μm.

FIG. 12a illustrates a schematic of two conjugates with different size: a covalent conjugate with Luc8 directly coupled to QD655 (20 nm), and a non-covalent complex with Luc8 binding to a streptavidin-coated QD655a (22 nm) meditated by a biotinylated NTA ligand. FIG. 12b illustrates the fluorescence spectra of two complexes at equal concentrations (5.5 pmol). FIG. 12c illustrates the bioluminescence emission spectra of two complexes at equal concentrations upon the addition of 1 μg coelenterazine.

FIG. 13a illustrates the bioluminescence emission spectra of QD655-Luc8 conjugates prepared at indicated QD655/Luc8 ratios. FIG. 13b illustrates the gel electrophoresis analysis of indicated QD655-Luc8 conjugates. FIG. 13c illustrates the BRET ratio of indicated conjugates calculated from their emission spectra in FIG. 13a.

FIG. 14a open without filters, and FIG. 14b with 650-660 nm filter. FIG. 14c illustrates fluorescence imaging of the same mouse injected with indicated solutions in FIG. 14a (excitation filter: 503-555 nm).

FIG. 17 illustrates the detection of MMP-2 with the BRET-based QD nanosensors.

FIG. 18A illustrates a NuPAGE assay. Lane 1 is the fusion Luc8 protein (size: 37.6 kD). Lane 2 is a MMP-2 treated fusion Luc8 protein (size 36.5 kD). Lane 3 is a mixture of 1 and 2. FIG. 18B illustrates a bioluminescence emission of the fusion protein before and after MMP-2 cleavage.

DETAILED DESCRIPTION

Figure 1:
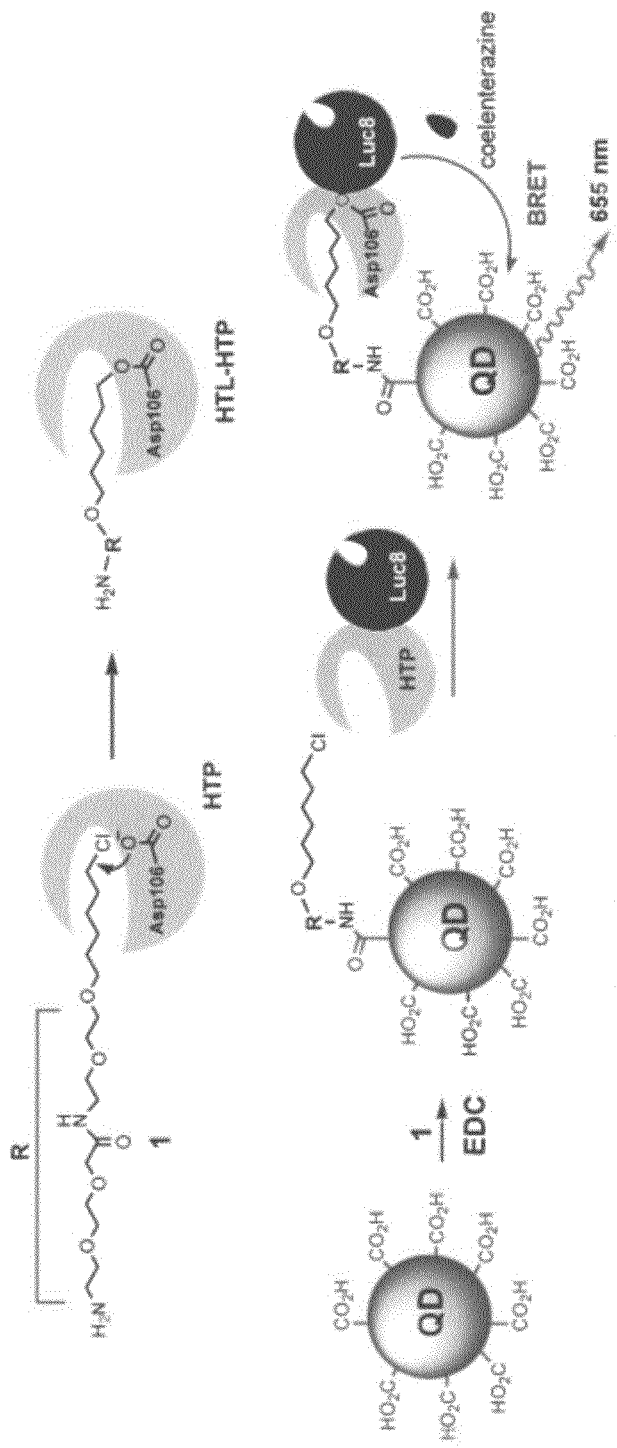
FIG. 1 illustrates scheme 1, which shows the specific conjugation of proteins to quantum dots mediated by the HaloTag protein and its ligand.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature. In particular, See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984), each of which is incorporated herein by reference.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

"Bioluminescent donor protein" refers to a protein capable of acting on a bioluminescent initiator molecule substrate to generate bioluminescence.

"Bioluminescent initiator molecule" is a molecule that can react with a bioluminescent donor protein to generate bioluminescence.

Bioluminescence (BL) is defined as emission of light by living organisms that is well visible in the dark and affects visual behavior of animals (See e.g., Harvey, E. N. (1952). Bioluminescence. New York: Academic Press; Hastings, J. W. (1995). Bioluminescence. In: Cell Physiology (ed. by N. Speralakis). pp. 651-681. New York: Academic Press.; Wilson, T. and Hastings, J. W. (1998). Bioluminescence. Annu Rev Cell Dev Biol 14, 197-230.). Bioluminescence does not include so-called ultra-weak light emission, which can be detected in virtually all living structures using sensitive luminometric equipment (Murphy, M. E. and Sies, H. (1990), Meth. Enzymol. 186, 595-610; Radotic, K, Radenovic, C, Jeremic, M. (1998), Gen Physiol Biophys 17, 289-308). Bioluminescence also does not include weak light emissions, which most probably do not play any ecological role, such as the glowing of bamboo growth cone (Totsune, H., Nakano, M., Inaba, H. (1993), Biochem. Biophys. Res Comm. 194, 1025-1029). Bioluminescence also does not include emission of light during fertilization of animal eggs (Klebanoff, S. J., Froeder, C. A., Eddy, E. M., Shapiro, B. M. (1979), J. Exp. Med. 149, 938-953; Schomer, B. and Epel, D. (1998), Dev Biol 203, 1-11). Each of the citations referenced above are incorporated herein by reference.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). In addition, the protein can include non-standard and/or non-naturally occurring amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homo-glutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptides as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in *Xenopus* oocytes by microinjection of mutated mRNA and chemically aminoacylated suppressor tRNAs (Turcatti, et al., J. Biol. Chem., 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., Biochem., 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Polynucleotide encompasses the terms "nucleic acid," "nucleic acid sequence," or "oligonucleotide" as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alias.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain. Codons correspond to specific amino acids (as defined by the transfer RNAs) or to start and stop of translation by the ribosome.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

As used herein, the terms "host" or "organism" include humans, mammals (e.g., cats, dogs, horses, etc.), living cells, and other living organisms, as well as samples such as tissue taken from a host or organism. A living organism can be as simple as, for example, a single eukaryotic cell or as complex as a mammal.

General Discussion

Embodiments of the present disclosure include conjugate systems, methods of using conjugate systems, self-illuminating quantum dot conjugates, systems including self-illuminating quantum dot conjugates, methods of using the self-illuminating quantum dot conjugates, and the like. In general, embodiments of the present disclosure involve the non-radiative transfer of energy between a bioluminescence donor molecule and a quantum dot without external illumination. In general, the bioluminescence donor molecule interacts with a bioluminescence initiating molecule to produce an emission. The non-radiative transfer of energy from the bioluminescence donor molecule to the quantum dots causes the quantum dot to emit radiation at a different wavelength that can be detected and measured using an appropriate detection system. In other words, bioluminescence resonance energy transfer (BRET) can take place between the bioluminescence donor molecule and the quantum dot. In this regard, embodiments of the present disclosure do not need an external light source to produce an emission from the quantum dot.

The conjugate (e.g., self-illuminating quantum dot conjugate) can be used to produce bioluminescent and/or fluorescent images. In addition, multiplexed imaging of one or more targets can be performed by using a plurality of self-illuminating quantum dot conjugates where each conjugate includes a quantum dot with distinct emission spectra. Further, embodiments of the present disclosure can produce bioluminescence at relatively longer wavelengths than currently used, which provides methods and systems of imaging in deep tissues.

It should also be noted that since the self-illuminating quantum dot conjugate does not need an external illumination source, the sensitivity is increased because the background signal-to-noise ratio increases. It should also be noted that the endogenous chromophores in the imaged tissue do not emit radiation in response to an external illumination source, where such radiation would decrease the signal-to-noise ratio.

In addition, the self-illuminating quantum dot conjugates are distinguishable and can be individually detected. In this regard, the self-illuminating quantum dot conjugates can be modified so that the self-illuminating quantum dot conjugates interact with certain targets or target compounds (e.g., chemical and/or biological compounds or polymers such a biomolecules, proteins, DNA, RNA, and the like), which allows detection of the target molecules (e.g., in-vivo) thereby determining the area in which the target molecules are located, for example. In an embodiment, the target can include, but is not limited to, a compound, a polypeptide, a polynucleotide, an antibody, an antigen, a hapten, a cell type, a tissue type, an agent (as described below), and the like Embodiments of the disclosure can be used in applications such as the following: cellular studies, in vivo cell trafficking, stem cell studies, tumor imaging, biomolecule array systems, biosensing, biolabeling, gene expression studies, protein studies, medical diagnostics, diagnostic libraries, microfluidic systems, delivery vehicles, multiplex imaging of multiple events substantially simultaneously, and high throughput assays for drug screening. For example, the self-illuminating quantum dot conjugates in combination with spectral imaging can be used for multiplexed imaging and detection (in vitro or in vivo) of polynucleotides, polypeptides, and the like, in a system, a host or single living cells. The self-illuminating quantum dot conjugates can be used to detect (and visualize) and quantitate events in a system, a host or a cell in in vitro as well as in in vivo studies, which decreases time and expenses since the same system can be used for cells and living organisms. For example, a drug being tested in cell culture with the self-illuminating quantum dot conjugates can then also be tested in living subjects using the same self-illuminating quantum dot conjugates.

Embodiments of the disclosure can be used to non-invasively measure selected events or interactions, the presence or absence of an agent (e.g., chemical and/or biological compounds or polymers), and the like at a depth in an animal from about less than 6 centimeters (cm), less than about 5 cm, less than about 4 cm, less than about 3 cm, less than about 2 cm, and less than about 1 cm. For example, the self-illuminating quantum dot conjugates can be used to measure cellular events in deep tissue.

In particular, the self-illuminating quantum dot conjugates can be used in in-vivo diagnostic and/or therapeutic applications such as, but not limited to, targeting diseases and/or conditions and/or imaging diseases and/or conditions. For example, one or more embodiments of the self-illuminating quantum dot conjugates can be used to identify the type of disease, locate the proximal locations of the disease, and/or deliver agents (e.g, drugs) to the diseased cells (e.g., cancer cells, tumors, and the like) in living animals.

As mentioned above, the self-illuminating quantum dot conjugate includes a bioluminescence donor molecule and a quantum dot. In the presence of the bioluminescence initiating molecule or compound, the bioluminescence initiating compound can react with the bioluminescence donor molecule. The reaction causes the bioluminescence donor molecule to emit bioluminescence energy. The non-radiative energy transfer from the bioluminescence donor molecule to the quantum dot can occur when there is an overlap (e.g., greater than 0.1%) between the emission and excitation spectra of the donor and acceptor molecules, respectively. It should be noted that the greater the overlap, the greater the efficiency. The energy is accepted by the quantum dot, and then the quantum dot emits fluorescent energy. The bioluminescence energy and/or the fluorescent energy can be detected and quantified in real time using an appropriate detection system (e.g., a photomultiplier tube in a fluorometer and/or a luminometer, for example).

In an embodiment, the self-illuminating quantum dot conjugate could be designed to degrade in the presence of certain agents. Therefore, the ratio of the bioluminescence energy and the fluorescent energy can be detected and quantified in real time to watch the self-illuminating quantum dot conjugate degrade. Thus, the presence of an agent (e.g., an agent present in a precancerous cell, cancer, and/or tumor, or some other disease) can be detected by observing the decay of the fluorescent energy emitted by the quantum dot because the BRET between the quantum dot and the bioluminescence donor molecule is reduced and/or eliminated.

In another embodiment, a conjugate system includes a bioluminescence donor molecule complex and a quantum dot complex. The bioluminescence donor molecule complex and the quantum dot complex are introduced to the system independently (e.g., as two separate complexes). The bioluminescence donor molecule complex includes a bioluminescence donor molecule, while the quantum dot complex includes a quantum dot. A target of interest modifies or combines with either the bioluminescence donor molecule complex or the quantum dot complex causing the two complexes to come in substantially close proximity (e.g., about 50 to 100 Angstroms), which would allow non-radiative energy transfer from the bioluminescence donor molecule to the quantum dot in the presence of the bioluminescence initiating molecule or compound. The term "substantially close proximity" includes distances that allow for non-radiative energy transfer from the bioluminescence donor molecule to the quantum dot in the presence of the bioluminescence initiating molecule or compound. In an embodiment, the complexes may associate with one another and remain as two separate complexes. In another embodiment, the complexes may self assemble into a single complex (e.g., a stable complex or one that could degrade under appropriate conditions such as those described herein). In another embodiment, the two complexes can form a single complex. The resulting bioluminescence donor molecule/quantum dot conjugate may be a stable molecule, or an entity that degrades with time or an external stimuli such as the presence of a chemical agent or a change in the surrounding environment that degrades the entity.

The reaction of the bioluminescence initiating molecule with the bioluminescence donor molecule causes the bioluminescence donor molecule to emit bioluminescence energy. The non-radiative energy transfer from the bioluminescence donor molecule to the quantum dot can occur when there is an overlap (e.g., greater than 0.1%) between the emission and excitation spectra of the donor and acceptor molecules, respectively. The energy is accepted by the quantum dot, and then the quantum dot emits fluorescent energy. The bioluminescence energy and/or the fluorescent energy can be detected and quantified in real time (e.g., in vivo or in vitro) using an appropriate detection system.

For example, a conjugate system includes a bioluminescence donor molecule complex and a quantum dot complex. The bioluminescence donor molecule complex and the quantum dot complex are introduced to the system independently (e.g., as two separate complexes). The bioluminescence donor molecule complex includes a bioluminescence donor molecule, while the quantum dot complex includes a quantum dot. One of the bioluminescence donor molecule complex or the quantum dot complex includes a first agent (e.g., protein) that has an affinity for a first target (e.g., protein). Upon interaction with the first agent, the first target undergoes a change to a second target (still having an affinity for the first agent or otherwise bound to the complex). The other of the bioluminescence donor molecule complex or the quantum dot complex includes a second agent that has an affinity for the second target so that the two complexes are attracted to one another. In other words, when one of the agents of a first complex interacts with a target of interest, the target undergoes a chemical, biological, and/or physical change. The second complex (other complex) includes an agent that has an affinity for the target after the chemical, biological, and/or physical change, so that the two complexes are attracted to one another.

The interaction causes the two complexes to come in substantially close proximity (e.g., 50 to 100 Angstroms), which would allow non-radiative energy transfer from the bioluminescence donor molecule to the quantum dot in the presence of the bioluminescence initiating molecule or compound. The term "substantially close proximity" includes distances that allow for non-radiative energy transfer from the bioluminescence donor molecule to the quantum dot in the presence of the bioluminescence initiating molecule or compound.

The reaction of the bioluminescence initiating molecule with the bioluminescence donor molecule causes the bioluminescence donor molecule to emit bioluminescence energy. The non-radiative energy transfer from the bioluminescence donor molecule to the quantum dot can occur when there is an overlap (e.g., greater than 0.1%) between the emission and excitation spectra of the donor and acceptor molecules, respectively. The energy is accepted by the quantum dot, and then the quantum dot emits fluorescent energy. The bioluminescence energy and/or the fluorescent energy can be detected and quantified in real time (e.g., in vivo or in vitro) using an appropriate detection system.

In another example, a conjugate system includes a bioluminescence donor molecule complex and a quantum dot complex. The bioluminescence donor molecule complex and the quantum dot complex are introduced to the system independently (e.g., as two separate complexes). The bioluminescence donor molecule complex includes a bioluminescence donor molecule, while the quantum dot complex includes a quantum dot. One of the bioluminescence donor molecule complex or the quantum dot complex includes a first agent (e.g., protein) that has an affinity for a first target (e.g., protein). Upon interaction with first target, the first agent undergoes a change to a second agent. The other of the bioluminescence donor molecule complex or the quantum dot complex includes a third agent that has an affinity for the second agent so that the two complexes are attracted to one another. In other words, when one of the agents of a first complex interacts with a target of interest, the agent or first complex undergoes a chemical, biological, and/or physical change. The second complex (other complex) includes an agent that has an affinity for the agent of the first complex or the first complex after the chemical, biological, and/or physical change, so that the two complexes are attracted to one another.

The interaction causes the two complexes to come in substantially close proximity (e.g., 50 to 100 Angstroms), which would allow non-radiative energy transfer from the bioluminescence donor molecule to the quantum dot in the presence of the bioluminescence initiating molecule or compound. The term "substantially close proximity" includes distances that allow for non-radiative energy transfer from the bioluminescence donor molecule to the quantum dot in the presence of the bioluminescence initiating molecule or compound.

The reaction of the bioluminescence initiating molecule with the bioluminescence donor molecule causes the bioluminescence donor molecule to emit bioluminescence energy. The non-radiative energy transfer from the bioluminescence donor molecule to the quantum dot can occur when there is an overlap (e.g., greater than about 0.1%) between the emission and excitation spectra of the donor and acceptor molecules, respectively. The energy is accepted by the quantum dot, and then the quantum dot emits fluorescent energy. The bioluminescence energy and/or the fluorescent energy can be detected and quantified in real time (e.g., in vivo or in vitro) using an appropriate detection system.

In another example, a conjugate system includes a bioluminescence donor molecule complex and a quantum dot complex. The bioluminescence donor molecule complex and the quantum dot complex are introduced to the system independently (e.g., as two separate complexes). The bioluminescence donor molecule complex includes a bioluminescence donor molecule, while the quantum dot complex includes a quantum dot. One of the bioluminescence donor molecule complex or the quantum dot complex includes a first agent (e.g., protein) that has an affinity for a first target (e.g., protein). Upon interaction with a second agent, the first target undergoes a change (e.g., chemical, biological, and/or physical change) to a second target (still having an affinity for the first agent). The other of the bioluminescence donor molecule complex or the quantum dot complex includes a third agent that has an affinity for the second target so that the two complexes are attracted to one another.

The interaction causes the two complexes to come in substantially close proximity (e.g., 50 to 100 Angstroms), which would allow non-radiative energy transfer from the bioluminescence donor molecule to the quantum dot in the presence of the bioluminescence initiating molecule or compound. The term "substantially close proximity" includes distances that allow for non-radiative energy transfer from the bioluminescence donor molecule to the quantum dot in the presence of the bioluminescence initiating molecule or compound.

The reaction bioluminescence initiating molecule with the bioluminescence donor molecule causes the bioluminescence donor molecule to emit bioluminescence energy. The non-radiative energy transfer from the bioluminescence donor molecule to the quantum dot can occur when there is an overlap (e.g., greater than 0.1%) between the emission and excitation spectra of the donor and acceptor molecules, respectively. The energy is accepted by the quantum dot, and then the quantum dot emits fluorescent energy. The bioluminescence energy and/or the fluorescent energy can be detected and quantified in real time (e.g., in vivo or in vitro) using an appropriate detection system. Additional details are described in Example 4.

In an illustrative embodiment, the detection system used to measure the signal from the self-illuminating quantum dot conjugate includes, but is not limited to, a light tight module and an imaging device disposed in the light tight module. The imaging device can include, but is not limited to, a CCD camera and a cooled CCD camera. It should be noted that other detection systems can be used to detect the bioluminescence energy and/or the fluorescent energy, such as, but not limited to, a fluorometer, a luminometer, a multiple well microplate reader, and the like.

In an embodiment, the self-illuminating quantum dot conjugates can be detected in a system (e.g., a bioluminescence resonance energy transfer (BRET) system) using a detection system having a cooled charge-coupled device (CCD) camera, for example, capable of imaging low quantum yield of visible light ranges from about 300 to 900 nm wavelength emitted from superficial and deep tissue structures of small living subjects.

Self-Illuminating Quantum Dot Conjugates

As indicated above, the self-illuminating quantum dot conjugate can include, but is not limited to, a bioluminescence donor molecule and a quantum dot. In an embodiment, the bioluminescence donor molecule is bound (e.g., associated directly or indirectly) with the quantum dot prior to introduction to a system or host, while in another embodiment the bioluminescence donor molecule and the quantum dot are not bound prior to introduction to a system or host. The term "bound" can include ways in which the bioluminescence donor molecule and the quantum dot interact with one another to form the self-illuminating quantum dot conjugate. In general, the bioluminescence donor molecule and the quantum dot can be bound to one another by a physical, biological, biochemical, and/or chemical association directly or indirectly by a suitable means. The term "bound" can include, but is not limited to, chemically bonded (e.g., covalently or ionically), biologically bonded, biochemically bonded, and/or otherwise associated with the quantum dot. In an embodiment, bound can include, but is not limited to, a covalent bond, a non-covalent bond, an ionic bond, a chelated bond, as well as being bound through interactions such as, but not limited to, hydrophobic interactions, hydrophilic interactions, charge-charge interactions, π-stacking interactions, combinations thereof, and like interactions. In an embodiment, the quantum dot has amine groups disposed on the surface of the quantum dot, and the bioluminescence donor molecule can conjugate with an amine group. The surface of the quantum dot can be coated with other compounds that have one or more functional groups that can conjugate with the bioluminescence donor molecule.

In general, a plurality of bioluminescence donor molecules is bound to the quantum dot. The number of bioluminescence donor molecules per quantum dot can be controlled, at least in part, by controlling the conjugation conditions, the surface of the quantum dot, the type of bioluminescence donor molecule, and the like. The number of bioluminescence donor molecules per quantum dot may be about 1 to 100, 1 to 75, 1 to 50, 1 to 30, 1 to 20, and 1 to 10. In an embodiment, the more bioluminescence donor molecules per quantum dot, the higher the emission intensity. Therefore, the number of bioluminescence donor molecules per quantum dot can be used to control the intensity of the quantum dot emission. Additional details about the bioluminescence donor molecule and the quantum dot are described below.

In an embodiment, the self-illuminating quantum dot conjugate or the bioluminescence donor molecule (or complex) and the quantum dot (or complex) can also include one or more types of agents bound (e.g., associated directly or indirectly) to the bioluminescence donor molecule and/or the quantum dot. The self-illuminating quantum dot conjugate or the bioluminescence donor molecule (or complex) and the quantum dot (or complex) can include one or more agents that can be used to enhance the interaction of the self-illuminating quantum dot conjugate with the host or subject. The agent can have an affinity for a target such as, but not limited to, a compound, a polypeptide, a polynucleotide, an antibody, an antigen, a hapten, a cell type, a tissue type, and the like. In an embodiment, the agent may be an antigen specific for an antibody that corresponds to a certain disease or condition. In another embodiment, the agent may be a first protein specific for another protein. In another embodiment, the agent may be a polynucleotide sequence specific for a complementary polynucleotide sequence. In another embodiment, the agent can undergo a chemical, biological, and/or physical change, where the changed agent can have an affinity for another agent or target.

The agent can include, but is not limited to, polypeptides (e.g., protein such as, but not limited to, an antibody (monoclonal or polyclonal)), nucleic acids (both monomeric and oligomeric), polysaccharides, sugars, fatty acids, steroids, purines, pyrimidines, drugs (e.g., small compound drugs), ligands, or combinations thereof. In an embodiment, the agent has an affinity for functional groups, compounds, cells, tissue, and the like, associated with a disease or condition. The agent can have an affinity for one or more targets.

In another embodiment, the agent can make the self-illuminating quantum dot conjugate or the bioluminescence donor molecule (or complex) and the quantum dot (or complex) bio-compatible. In other words, the self-illuminating quantum dot conjugate can include a bio-compatibility compound. The bio-compatibility compound can include compounds such as, but not limited to, polyethylene glycol; polypropylene glycol 500, dextran, and derivatives thereof. The bio-compatibility compound can be attached directly or indirectly with the quantum dot and/or an agent bound to the quantum dot.

Thus, the agent can be selected so that the self-illuminating quantum dot conjugate can be used to image and/or diagnose the presence or absence of the compounds, polypeptides, polynucleotides, antibodies, antigens, haptens, cell types, tissue types, and the like, associated with a disease or condition, or related biological activities.

In addition, the agent can also include, but is not limited to, a drug, a therapeutic agent, radiological agent, a small molecule drug, and combinations thereof, that can be used to treat the target molecule and/or the associated disease and condition of interest. The drug, therapeutic agent, and radiological agent can be selected based on the intended treatment as well as the condition and/or disease to be treated. In an embodiment, the self-illuminating quantum dot conjugate can include two or more agents used to treat a condition and/or disease.

In an embodiment, the self-illuminating quantum dot conjugate or the bioluminescence donor molecule (or complex) and the quantum dot (or complex) can include at least two different types of agents, one being a targeting agent that targets certain cells or compounds associated with a condition and/or disease, while the second agent is a drug used to treat the disease. In this manner, the self-illuminating quantum dot conjugate acts as a detection component, a delivery component to the cells of interest, and a delivery component for the treatment agent. The detection of the self-illuminating quantum dot conjugate can be used to ensure the delivery of the drug to its intended destination as well as the quantity of self-illuminating quantum dot conjugates delivered to the destination.

Quantum Dot

As indicated above, the self-illuminating quantum dot conjugate can include quantum dots such as, but not limited to, luminescent semiconductor quantum dots. In general, quantum dots include a core and a cap, however, uncapped quantum dots can be used as well. The "core" is a nanometer-sized semiconductor. While any core of the IIA-VIA, IIIA-VA, or IVA-IVA, IVA-VIA semiconductors can be used in the context of the present disclosure, the core is preferably, upon combination with a cap, a result in a luminescent quantum dot. A IIA-VIA semiconductor is a compound that contains at least one element from Group IIA and at least one element from Group VIA of the periodic table, and so on. For example, the core can be Au, CdS, CdSe, CdTe, ZnSe, ZnS, PbS, PbSe, or an alloy. It should also be noted that a quantum dot composite including a quantum dot can be used as well (e.g., a hybrid of magnetic nanoparticle with quantum dots, a carbon nanotube hybrid with quantum dots, and the like).

The core can include two or more elements. In one embodiment, the core is a IIA-VIA, IIIA-VA, or IVA-IVA semiconductor that ranges in size from about 1 nanometer (nm) to 40 nm, about 1 nm to 30, about 1 nm to 20 nm, and about 1 nm to 10 nm. In another embodiment, the core is more preferably a IIA-VIA semiconductor and ranges in size from about 2 nm to 10 nm.

The "cap" is a semiconductor that differs from the semiconductor of the core and binds to the core, thereby forming a surface layer on the core. The cap can be such that, upon combination with a given semiconductor core, a luminescent quantum dot results. The cap should passivate the core by having a higher band gap than the core. In one embodiment, the cap is a IIA-VIA semiconductor of high band gap. Combinations of the core and cap can include, but are not limited to the following: the cap is ZnS when the core is CdSe or CdS, and the cap is CdS when the core is CdSe. Other exemplary quantum dots include, but are not limited to, CdS, ZnSe, CdSe, CdTe, $CdSe_xTe_{1-x}$, InAs, InP, PbTe, PbSe, PbS, HgS, HgSe, HgTe, CdHgTe, and GaAs. The cap is about 0.1 to 10 nm, about 0.1 to 5 nm, and about 0.1 to 2 nm.

The wavelength emitted (i.e., color) by the quantum dots can be selected according to the physical properties of the quantum dots, such as the size and the material of the nanocrystal. Quantum dots are known to emit light from about 300 nm to 2000 nm (e.g., UV, near IR, and IR). The colors of the quantum dots include, but are not limited to, red, blue, green, and combinations thereof. The color or the fluorescence emission wavelength can be tuned continuously. The wavelength band of light emitted by the quantum dot is determined by either the size of the core or the size of the core and cap, depending on the materials that make up the core and cap. The emission wavelength band can be tuned by varying the composition and the size of the QD and/or adding one or more caps around the core in the form of concentric shells.

The intensity of the color of the quantum dots can be controlled. For each color, the use of 10 intensity levels (0, 1, 2, ... 9) gives 9 unique codes, because level "0" cannot be differentiated from the background. The number of codes increases exponentially for each intensity and each color used. For example, a three color and 10 intensity scheme yields 999 codes, while a six color and 10 intensity scheme has a theoretical coding capacity of about 1 million.

In general, it is more advantageous to use more colors, rather than more intensity levels, in order to increase the number of usable codes. The number of intensities is preferably from 0 to 20, more preferably about 1 to 10. The number of colors is preferably about 1 to 10 (e.g., 2-8), and more preferably, about 3 to 7. By the term "multicolor quantum dot," it is meant that more than one color of luminescent quantum dots is associated with the same agent. For example two self-illuminating quantum dot conjugates with different colored quantum dots are bound to the same agent, so that both emit radiation when in contact with the particular agent.

Quantum dots and the synthesis of quantum dots is well known and is described in U.S. Pat. Nos. 5,906,670; 5,888,885; 5,229,320; 5,482,890; 6,468,808; 6,306,736; 6,225,198; 6,906,339; 6,905,766; 6,846,475; 6,743,400; 6,623,559; 6,528,165; 6,967,112; 6,794,265; 6,730,531; 6,633,370; 5,989,947; 5,532,184; 5,202,290; and 5,170,226, (all of which are incorporated herein by reference) and in many research articles. The wavelengths emitted by quantum dots and other physical and chemical characteristics have been described in U.S. Pat. No. 6,468,808 and the like, and will not be described in any further detail. In addition, methods of preparation of quantum dots are described in U.S. Pat. No. 6,468,808 and the like, and will not be described any further detail.

Bioluminescence Donor Molecule

The bioluminescence donor molecule can include, but is not limited to, luciferases, *Renilla* Luciferase, firefly Luciferase, aquorin, click beetle Luciferase, Gaussia Luciferase, horse radish peroxidase, and other bioluminescence donor molecules than can work with quantum dots, and combinations thereof. In addition, the bioluminescence donor molecule can include molecules as described in PCTUS06/34601 (entitled "Luciferases And Methods For Making And Using The Same", filed on Sep. 6, 2006), which is incorporated herein by reference in its entirety.

In an embodiment, the bioluminescence donor molecule can include, but is not limited to, a *Renilla* Luciferase protein (as described herein and in the example) (Rluc, SEQ ID NO:1), a mutated *Renilla* Luciferase protein (as described herein and in the example) (Rluc8, SEQ ID NO:2), conservatively modified variants of each, and combinations thereof. The mutated *Renilla* Luciferase protein can include, but is not limited to, 8 mutations in the sequence, and these include A55T, C124A, S130A, K136R, A143M, M185V, M253L, and S287L (e.g., as described herein and in the example). In addition, the mutated *Renilla* Luciferase protein can include conservatively modified variants of one or more of these mutations as long as the conservatively modified variant retains the characteristics of the mutated *Renilla* Luciferase protein.

In an embodiment, when the bioluminescence donor molecule is a mutated *Renilla* Luciferase protein, the bioluminescence sensitivity increase of about 20 to 60 fold or more and about 40 fold can be realized. Also in embodiments using the mutated *Renilla* Luciferase protein, the mutated *Renilla* Luciferase protein is more stable relative to other proteins.

In general, the mutated *Renilla* Luciferase protein is very stable. It has been shown that a C124A mutation increases the stability of RLuc. In order to further enhance the stability of RLuc, a number of mutations can be included in addition to the C124A mutation. The combination of 8 favorable mutations including C124A generated a mutant *Renilla* luciferase (RLuc8) that exhibited a greater than 150-fold stability improvement in murine serum when compared to native Rluc (<1 hr versus>100 hr) and increased the sensitivity of the system by about 20 to 60 fold and about 40 fold relative to native *Renilla* Luciferase. In addition to being more stable, RLuc8 also exhibited at least a 4-fold improvement in light output, along with red shift of about 5 nm to its emission spectrum with respect to the native Rluc. The *Renilla* Luciferase protein and the mutated *Renilla* Luciferase protein are described in more detail in the Examples and in Nature Biotechnology 2006 (See, So M-K, Xu C, Loening A M, Gambhir S S, Rao J. Self-illuminating quantum dot conjugates for in vivo imaging. *Nature Biotechnology* 2006; 24: 339-343 and PCT Application filed on Mar. 10, 2006 having PCT/US06/08632 and entitled "BIOLUMINESCENCE RESONANCE ENERGY TRANSFER (BRET) SYSTEMS AND METHODS OF USE THEREOF", and PCT Application filed on Sep. 6, 2006 having PCT/US2006/034601 and entitled "LUCIFERASES AND METHODS FOR MAKING AND USING THE SAME", each of which are incorporated herein by reference).

The agent and/or bioluminescence donor molecule can be linked to the quantum dot using any stable physical and/or chemical association to the quantum dot directly or indirectly. In general, the agent and/or bioluminescence donor molecule can be linked to the quantum dot using, but not limited to, a covalent link, a non-covalent link, an ionic link, a chelated link, as well as being linked to the quantum dot through interactions such as, but not limited to, hydrophobic interactions, hydrophilic interactions, charge-charge interactions, π-stacking interactions, combinations thereof, and like interactions. In embodiments a linker can be used to link the one or more of the components (e.g., the quantum dot, the bioluminescence donor molecules agent an the like).

The linker can be a compound that includes one or more functional groups to attach one or more of the quantum dot, the agent, bioluminescence donor molecule, and/or other components of the self-illuminating quantum dot conjugate. The linker can include functional groups such as, but not limited to, amines, carboxylic acids, hydroxyls, thios, and combinations thereof. The linker can include compounds such as, but not limited to, DTPA, EDTA, DOPA, EGTA, NTA, and combinations thereof.

Bioluminescence Initiating Compound

As mentioned above, the self-illuminating quantum dot conjugate is used in conjunction with a bioluminescence initiating compound to produce a radiation emission that is absorbed by the quantum dot. The bioluminescence initiating compound can include, but is not limited to, coelenterazine, analogs, and functional derivatives thereof, and D-luciferin analogs, and functional derivatives thereof. Derivatives of coelenterazine include, but are not limited to, coelenterazine 400a, coelenterazine cp, coelenterazine f, coelenterazine fcp, coelenterazine h, coelenterazine hcp, coelenterazine ip, coelenterazine n, coelenterazine O, coelenterazine c, coelenterazine c, coelenterazine i, coelenterazine icp, coelenterazine 2-methyl, and deep blue coelenterazine (DBC) (described in more detail in U.S. Pat. Nos. 6,020,192; 5,968,750 and 5,874,304, which are incorporated herein by reference). In an embodiment, the bioluminescence initiating compound can be D-luciferine when the bioluminescence compound is firefly luciferase.

In general, coelenterazines are known to luminesce when acted upon by a wide variety of bioluminescent proteins, specifically luciferases. Coelenterazines disclosed in U.S. patent application Ser. No. 10/053,482, filed Nov. 2, 2001 (which is hereby incorporated by reference in its entirety), could be used as well. Coelenterazines are available from Promega Corporation, Madison, Wis. and from Molecular Probes, Inc., Eugene, Oreg. Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997, which are incorporated herein by reference.

Methods of Use

As mentioned above, the present disclosure relates generally to methods for studying (e.g., detecting, localizing, or quantifying) cellular events, in vivo cell trafficking, stem cell studies, tumor imaging, biomolecule array systems, biosensing, biolabeling, gene expression studies, protein studies, medical diagnostics, diagnostic libraries, microfluidic systems, and delivery vehicles. The present disclosure also relates to methods for multiplex imaging of multiple events substantially simultaneously inside a subject (e.g., a host living cell, tissue, or organ, or a host living organism) using one or more self-illuminating quantum dot conjugates without the use of an external excitation source for the quantum dot. It should be noted that the bioluminescence donor molecule (or complex) and the quantum dot (or complex) can be used in methods using the self-illuminating quantum dot conjugates.

In short, the self-illuminating quantum dot conjugates are introduced to the subject using known techniques. The self-illuminating quantum dot conjugates can also be labeled with one or more types of agents for the particular study (e.g., agents directed to cancer imaging and/or treatment), as mentioned above. In addition, a single agent can be associated with two or more types of self-illuminating quantum dot conjugates, where the self-illuminating quantum dot conjugates include different quantum dots.

At an appropriate time (e.g., before, after, or at the same time as the self-illuminating quantum dot conjugate), the bioluminescence initiating compound is introduced to the host living cell, tissue, or organ, or a host living organism. In an embodiment, the appropriate time may include a time frame to allow unassociated self-illuminating quantum dot conjugates to be sufficiently cleared from the appropriate area, region, or tissue of interest. The bioluminescence initiating compound can react with the bioluminescence donor molecule. The reaction causes the bioluminescence donor molecule to emit bioluminescence energy. The energy transfer from the bioluminescence donor molecule to the quantum dot can occur when there is an overlap between the emission and excitation spectra of the donor and acceptor molecules, respectively. The energy is accepted by the quantum dot, and then the quantum dot emits fluorescent energy. The bioluminescence energy and/or the fluorescent energy can be detected and quantified in real time using a detection system. The measured signal is or can be correlated to the feature being studied. In an embodiment, the detection of the bioluminescence energy and/or the fluorescent energy can be conducted after a sufficient time frame to allow unassociated self-illuminating quantum dot conjugates to be sufficiently cleared from the appropriate area, region, or tissue of interest.

In an embodiment, the self-illuminating quantum dot conjugates can be used to study, image, diagnose the presence of, and/or treat cancerous cells, precancerous cells, cancer, or tumors. It should be noted that self-illuminating quantum dot conjugate can include agents specific for other diseases or conditions so that other diseases or conditions can be imaged, diagnosed, and/or treated using embodiments of the present disclosure. In an embodiment, other diseases and/or conditions can be studied, imaged, diagnosed, and/or treated in a manner consistent with the discussion below as it relates to cancerous cells, precancerous cells, cancer, and/or tumors.

In an embodiment, the self-illuminating quantum dot conjugates can be used to study, image, diagnose the presence of, and/or treat cancerous cells, precancerous cells, cancer, or tumors. The self-illuminating quantum dot conjugates include an agent that can be degraded in the presence of one or more components present with cancerous cells, precancerous cells, cancer, or tumors. When the agent degrades the self-illuminating quantum dot conjugate, the quantum dot does not emit a fluorescent energy. In other words, the self-illuminating quantum dot conjugate initially emits a fluorescent energy from the quantum dot, but the emission decays as the component degrades the polypeptide, which causes the self-illuminating quantum dot conjugate to degrade into multiple components (e.g., quantum dot and bioluminescence donor molecule). It should be noted that other diseases and/or conditions could be studied, imaged, diagnosed, and/or treated in a manner consistent with the discussion above.

For example, a polypeptide sequence (or other linker) can be placed between the quantum dot and the bioluminescence donor molecule. The polypeptide degrades in the presence of a component present with cancerous cells, precancerous cells, cancer, or tumors. Therefore, the self-illuminating quantum dot conjugate initially emits a fluorescent energy from the quantum dot, but the emission decays as the component degrades the polypeptide, which causes the self-illuminating quantum dot conjugate to degrade into multiple components. Additional details are discussed in Example 3.

In an embodiment, the self-illuminating quantum dot conjugate can include one or more agents that has an affinity for cancerous cells, precancerous cells, cancer, or tumors, so that upon introduction to the subject, the self-illuminating quantum dot conjugates coordinate with the cancerous cells, precancerous cells, cancer, or tumors. A bioluminescence initiating compound can be introduced to the subject and react with the bioluminescence donor molecule to produce an emission from the quantum dot. Thus, upon measuring the emitted energy from the quantum dot and/or the bioluminescence donor molecule, one can image and/or diagnose the presence of the cancerous cells, precancerous cells, cancer, or tumors.

In another embodiment, the self-illuminating quantum dot conjugate includes one or more agents to treat the cancerous cells, precancerous cells, cancer, or tumors. A bioluminescence initiating compound can be introduced to the subject and react with the bioluminescence donor molecule to produce an emission from the quantum dot. Thus, upon measuring the emitted energy from the quantum dot and/or the bioluminescence donor molecule, one can determine if the self-illuminating quantum dot conjugate has coordinated with the cancerous cells, precancerous cells, cancer, or tumors. Embodiments of the self-illuminating quantum dot conjugate can aid in visualizing the response of the cancerous cells, precancerous cells, cancer, or tumors to the agent.

In another embodiment, the self-illuminating quantum dot conjugate can include one or more coordinating agents that has an affinity for cancerous cells, precancerous cells, cancer, or tumors as well as one or more treating agents to treat the cancerous cells, precancerous cells, cancer, or tumors. A bioluminescence initiating compound can be introduced to the subject and react with the bioluminescence donor molecule to produce an emission from the quantum dot. Thus, upon measuring the emitted energy from the quantum dot and/or the bioluminescence donor molecule, one can image the cancerous cells, precancerous cells, cancer, or tumors as well as determine what portions of the cancerous cells, precancerous cells, cancer, or tumors are being treated by the treatment agent.

In general, the self-illuminating quantum dot conjugates can be used in a screening tool to select agents for imaging, diagnosing, and/or treating a disease or condition. In an embodiment, the self-illuminating quantum dot conjugates can be used in a screening tool to select agents for imaging, diagnosing, and/or treating cancerous cells, precancerous cells, cancer, or tumors. The self-illuminating quantum dot conjugates can be imaged and it can be determined if each agent can be used to image, diagnose, and/or treat cancerous cells, precancerous cells, cancer, or tumors.

Kits

This disclosure encompasses kits that include, but are not limited to, self-illuminating quantum dot conjugates (e.g., with one or more agents as described above), a bioluminescence initiating compound, and directions (written instructions for their use). In another embodiment, the kits include, but are not limited to, bioluminescent donor compounds (complex), quantum dot conjugates (complex) (e.g., with one or more agents as described above), a bioluminescence initiating compound, and directions (written instructions for their use). The components listed above can be tailored to the particular cellular event being studied and/or treated (e.g., cancer, cancerous, or precancerous cells). The kit can further include appropriate buffers and reagents known in the art for administering various combinations of the components listed above to the host cell or host organism.

EXAMPLES

Now having described the embodiments of the self-illuminating quantum dot conjugates, systems, and methods of use, in general, examples 1-4 describe some additional embodiments of the self-illuminating quantum dot conjugates, systems, and methods of use. While embodiments of self-illuminating quantum dot conjugates, systems, and methods of use are described in connection with examples 1-4 and the corresponding text and figures, there is no intent to limit embodiments of the self-illuminating quantum dot conjugates, systems, and methods of use to this description. On the contrary, the intent is to cover all alternatives, modifications, and equivalents included within the spirit and scope of embodiments of the present disclosure.

Example 1

Discussion

This example provides an embodiment of a conjugation method that utilizes a genetically engineered hydrolase to covalently immobilize a bioluminescent protein at the quantum dot surface. The immobilized bioluminescent protein can efficiently produce chemical energy to excite quantum dots via resonance energy transfer.

An embodiment of a method employs a commercially available, engineered haloalkane dehalogenase—the HaloTag protein (HTP) (See, Technical Manual, Promega, "HaloTag™ Interchangeable Labeling Technology"; http://www-.promega.com, 2006, which is incorporated herein by reference). The native enzyme is a monomeric protein (MW ~33 KDa) that cleaves carbon halogen bonds in aliphatic halogenated compounds. Upon the nucleophilic attack to Asp106 in the enzyme by the chloroalkane, an ester bond is formed between the HaloTag ligand and the protein (FIG. 1, Scheme 1). HTP contains a critical mutation in the catalytic triad (His272 to Phe) so that the formed ester bond between HTP and HaloTag ligand cannot be further hydrolyzed (FIG. 1, Scheme 1). HaloTag ligands labeled with small organic dyes such as coumarin and fluorescein have been developed for in vivo labeling of target proteins. This technology is applied for the specific conjugation of proteins to quantum dots.

To take advantage of this specific protein-ligand interaction, quantum dots can be functionalized with HaloTag ligands. A protein target can in turn be genetically fused to HTP at either its N- or C-terminus. The resulting fusion protein can then be conjugated to quantum dots through the reaction between HaloTag ligands and HTP (FIG. 1, Scheme 1).

To demonstrate the utility of this method for quantum dot conjugation, a bioluminescent protein, *Renilla* luciferase, was selected as the target. It was demonstrated that when *Renilla* luciferase is conjugated to quantum dots, bioluminescence resonance energy transfer (BRET) can take place (See, M.-K. So, C. Xu, A. M. Loening, S. S. Gambhir, J. Rao, *Nature Biotechnol.* 2006, 24, 339-343, which is incorporated herein by reference). Such quantum dot conjugates can emit light without light excitation, and offer greatly improved sensitivity for in vivo imaging. With *Renilla* luciferase as the target protein for the conjugation, the conjugation reaction can be conveniently evaluated from the BRET emission of the quantum dots—a measure of both the conjugation chemistry and the function of the conjugated luciferase.

Figure 3:
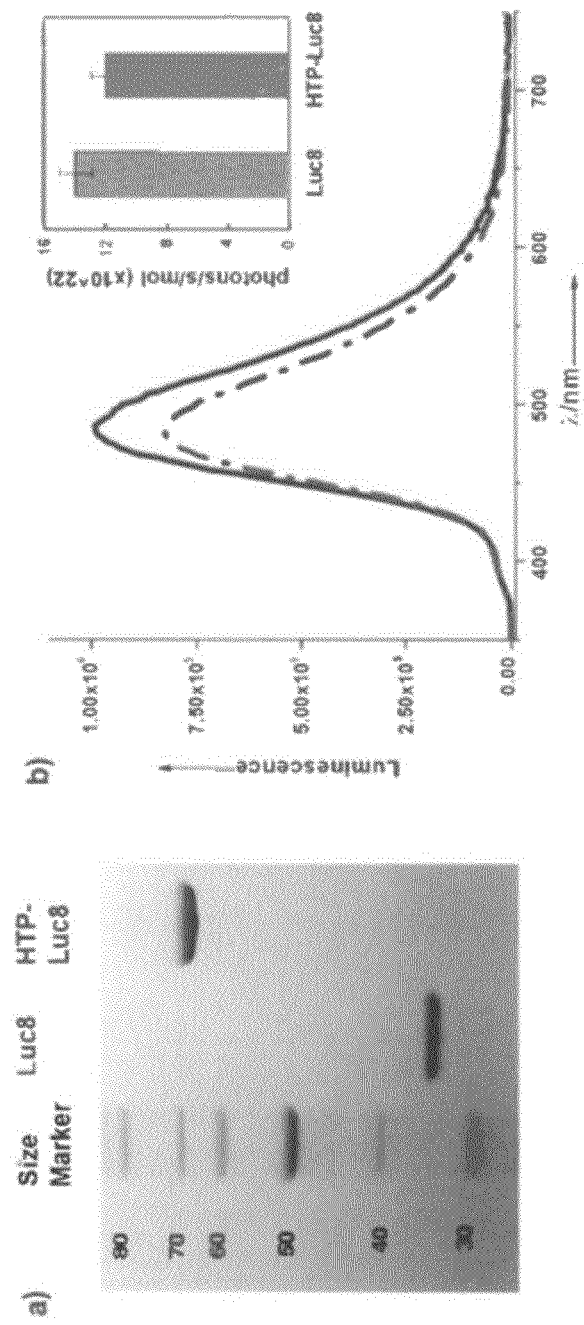
FIGS. 3a and 3b illustrate the characterization of the size and function of the fusion protein.

A stabilized mutant of *Renilla* luciferase (Luc8) was genetically fused to the N-terminus of the HTP and expressed to obtain the fusion protein HTP-Luc8. The C-terminus of HTP-Luc8 contained a 6xHis tag to facilitate its purification. Gel electrophoresis analysis indicated that the molecular weight of the fusion protein was consistent with the expected value, ~70 kDa (FIG. 3a). The bioluminescence activity of the fusion protein was estimated to be $1.2 \times 10^{23}$ photons/s/mole, ~86% of Luc8 (FIG. 3b).

In order to minimise potential steric hindrance between the quantum dots and HaloTag proteins during conjugation, a HaloTag ligand was designed containing an amino ethylene glycol group that would help present the ligand away from the quantum dot surface (FIG. 1, Scheme 1). The HaloTag ligand 1 was prepared from 6-chloro-1-iodohexane and 2-(2-aminoethoxy)ethanol by following the synthetic route outlined in FIG. 2, Scheme 2, and was immobilized through its amino group to the carboxylate-presenting quantum dots (QD@COOH). The resulting quantum dots coated with the HaloTag ligand 1 (QD@1) showed good solubility in neutral pH buffer. The conjugation of the fusion protein HTP-Luc8 to QD@1 was carried out by a simple mixing of both at 37° C., resulting in an irreversible covalent bond formation between ligand 1 on quantum dots and HTP-Luc8.

Figure 4:
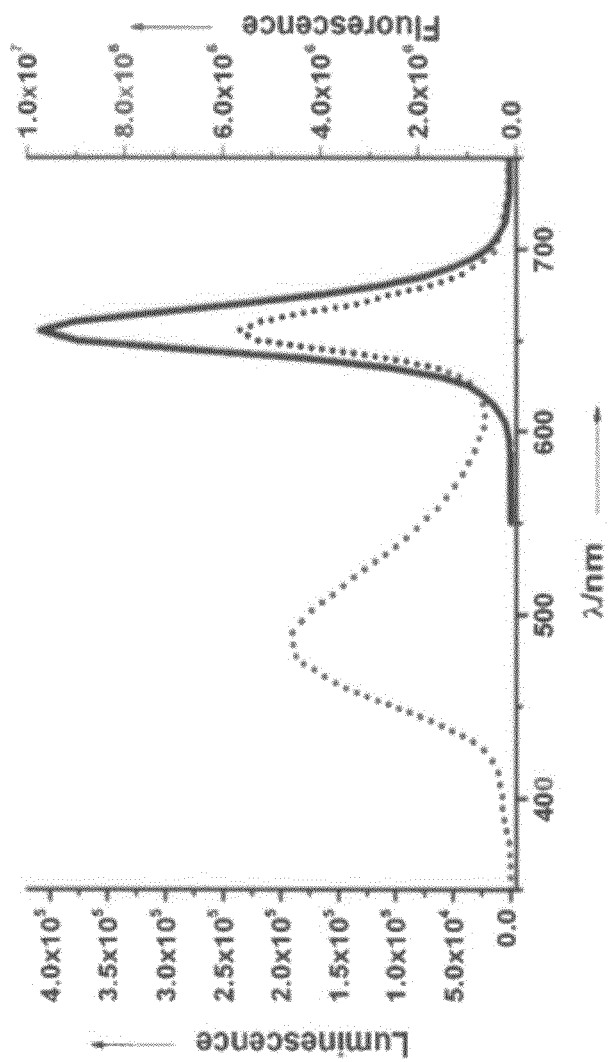
FIG. 4 illustrates the bioluminescence (black line) and fluorescence (dash grey line) spectra of conjugate QD@1-HTP-Luc8 in borate buffer. The fluorescence emission was collected with excitation at 480 nm.

Since successful immobilization of HTP-Luc8 to quantum dots should allow BRET to occur, the BRET emission was measured from the quantum dots following the conjugation reaction. Addition of coelenterazine, the substrate for *Renilla* luciferase, to the purified conjugate QD@1-HTP-Luc8 resulted in a dual-peak bioluminescence emission spectrum. In addition to the Luc8 peak at 480 nm, there was an emission maximum at 655 nm that overlapped well with the fluorescence emission of the quantum dot conjugates excited at 480 nm (FIG. 4).

Figure 5:
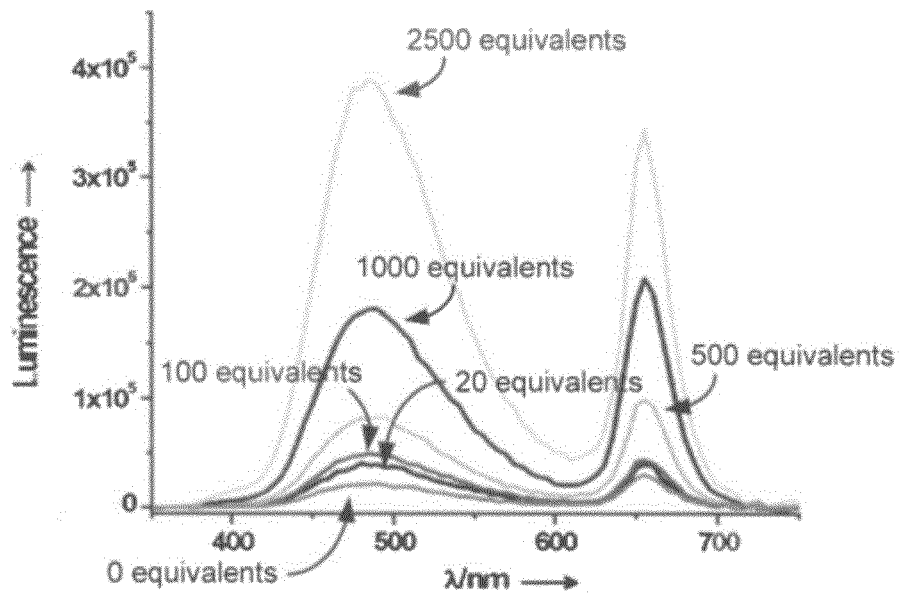
FIGS. 5 and 6 illustrate the dependence of the conjugation on the ligand 1.
Figure 6:
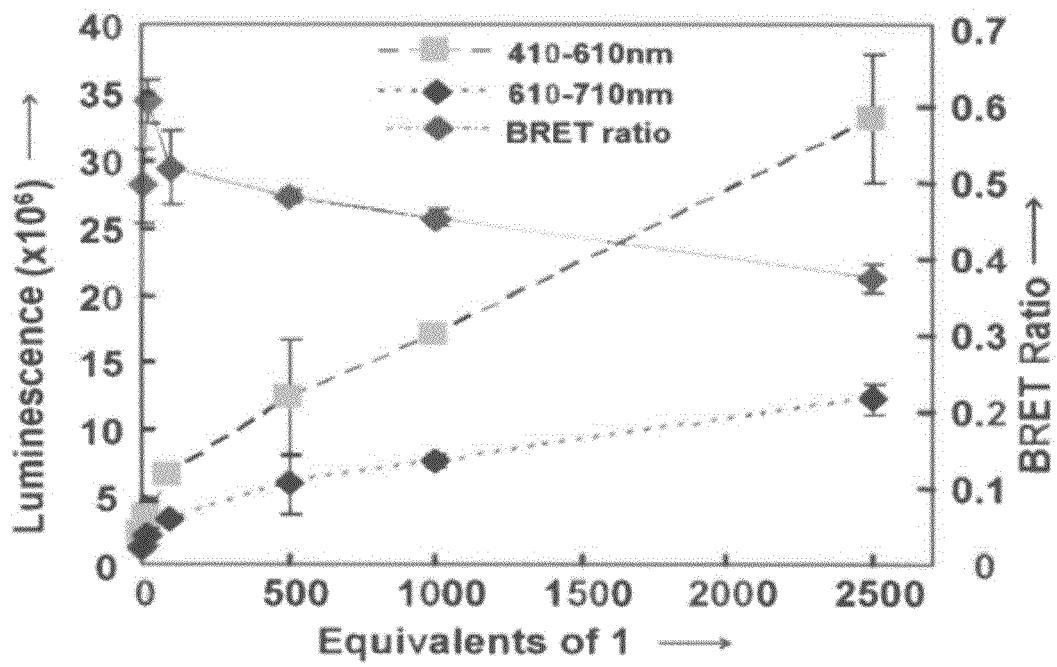

To evaluate whether the observed BRET emission was due to specific conjugation between the quantum dots and fusion proteins, the dependence of the BRET emission on the HaloTag ligand 1 used in the conjugation was examined. QD@COOH was first functionalized with various concentrations of 1. These modified quantum dots were subsequently conjugated with 20 equivalents of HTP-Luc8. FIGS. 5 and 6 show that with increasing amounts of ligand 1 used in the conjugation, the bioluminescence emissions from both the immobilized HTP-Luc8 and the quantum dots via BRET increased. When quantum dots without HaloTag ligand 1 attached were similarly mixed with the fusion protein, there were only a small emission from HTP-Luc8 at 480 nm and a small BRET emission from the quantum dots. The small BRET emission probably arises from an electrostatic interaction between the 6xHis tag on HTP-Luc8 and the negative carboxylate groups on the quantum dots. These results confirm that the BRET emission reflects specific conjugation occurring between the quantum dots and the fusion protein HTP-Luc8, and that the conjugation does not affect the enzymatic activity of the fusion protein HTP-Luc8.

The efficiency of the resonance energy transfer process can be quantitatively estimated from the BRET ratio. The BRET ratio is defined by the acceptor emission relative to the donor emission (See, M.-K. So, C. Xu, A. M. Loening, S. S. Gambhir, J. Rao, Nature Biotechnol. 2006, 24, 339-343, K. D. G. Pfleger, K. A. Eidne, Nat. Methods 2006, 3, 165-174, which are incorporated herein by refrence). In the quantum dot and HTP-Luc8 conjugate, the donor is Luc8 and the acceptor is quantum dots. The BRET ratio was calculated by dividing the total emission from the quantum dots by the total emission from HTP-Luc8, shown in FIG. 5b. With the increase in the number of HaloTag ligand 1 and, in turn, the increase in immobilized fusion protein, the BRET ratio decreased gradually from 0.6 to 0.4. In principle, the BRET ratio should not depend on the number of immobilized proteins if the BRET distance remains unchanged. This small decrease in the BRET ratio may be due to a shift in the orientation of the conjugated fusion proteins on the quantum dot surface (A larger number of immobilized proteins would lead to denser packing at the surface, resulting in the Luc8 domain of the fusion proteins being pushed further away from the quantum dot surface and consequently a larger average BRET distance).

Figure 7:
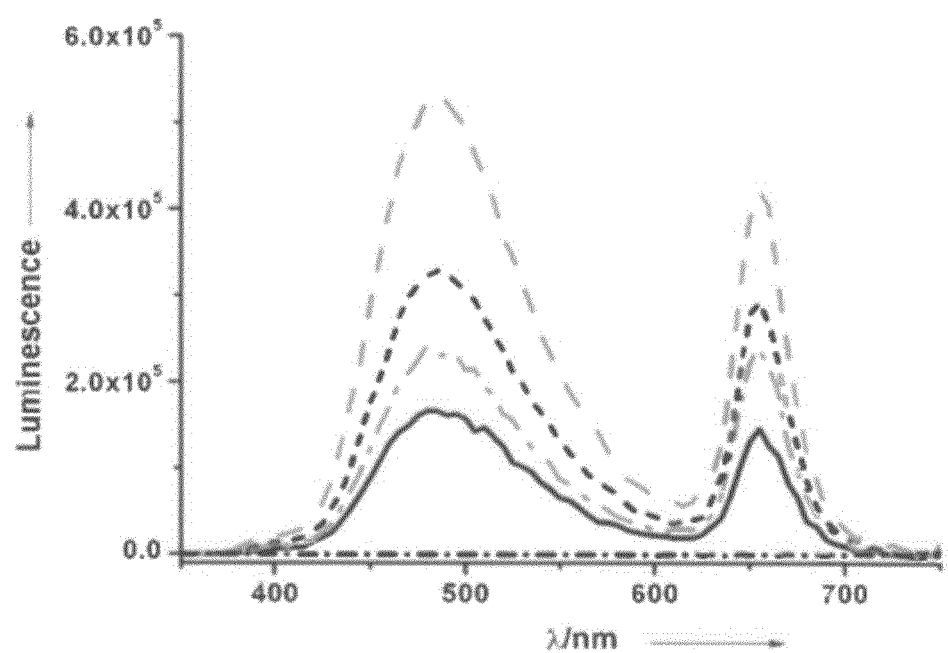
FIG. 7 illustrates the bioluminescence emission spectra of quantum dots conjugated with HTP-Luc8 (from top to bottom: 100, 50, 20, 10 equivalents) or 20 equivalents of Luc8. The quantum dots were reacted with 1000 equivalents of HaloTag ligand 1 before the conjugation with HTP-Luc8. Unconjugated proteins were removed by filtration before measurement.

Finally, the dependence of the conjugation reaction on the amount of fusion protein present was examined. Quantum dots were reacted with 1000 equivalents of HaloTag ligand 1, and then reacted with increasing concentrations of HTP-Luc8. As expected, the resulting conjugates showed increasing bioluminescence emissions both from HTP-Luc8 and from the quantum dots (FIG. 7). As a control, Luc8 (without HTP fusion) was incubated with the QD@1. The control reaction showed no bioluminescence emission, indicating no immobilization of Luc8 on the quantum dots and further confirming that the conjugation between quantum dots and HTP-Luc8 was specific.

In summary, this example describes embodiments based on the specific interaction between the HaloTag protein and its ligand, to functionalize quantum dots for biological imaging. Using this method, a bioluminescent protein was conjugated to quantum dots and produced self-illuminating quantum dot conjugates.

Materials and Methods

Chemicals for HaloTag ligand synthesis were from Sigma-Aldrich. The coupling reagent 1-ethyl-3-(3-dimethylaminopropyl)carbodiimide hydrochloride (EDC) was from Fluka. Quantum dots were purchased from Invitrogen, and have CdSe/ZnS core-shell structures with a quantum yield (determined in 50 mM pH 9 borate buffer) of 83%. Coelenterazine was from Prolume. The plasmid pHT2 (HaloTag) was from Promega. NanoSep 100K filters for quantum dot purification were from Pall, Life Science.

Figure 2:
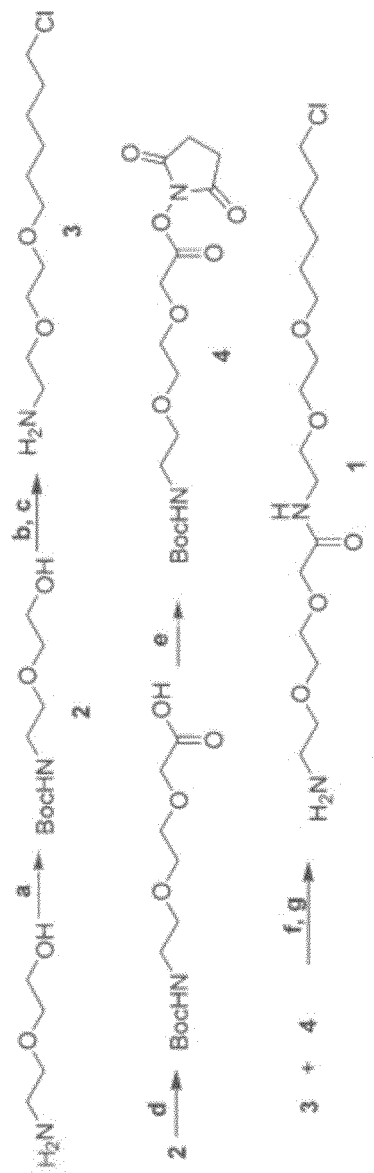
FIG. 2 illustrates scheme 2, which shows the synthesis of HaloTag ligand 1. Reagent and conditions: a. Boc2O/EtOH, 0° C., 2 hr; b. NaH/DMF-THF and 6-chloro-1-iodohexane; c. TFA/anisole in DCM; d. NaH/DMF-THF and iodoacetic acid sodium salt; e. N-Hydroxysuccinimide and DCC in DCM; f. DIPEA/THF; and g. TFA/anisole in DCM.

Synthesis of 1: the compound was synthesized from 6-chloro-1-iodohexane and 2-(2-aminoethoxy)ethanol according to FIG. 2, Scheme 2. $^1$H NMR: (400 MHz, CDCl$_3$) δ 3.92 (s, 2H), 3.70-3.20 (m, 18H), 2.09 (m, 2H), 2.64 (m, 2H), 2.50 (m, 2H), 1.40-1.20 (s, 4H). LC-MS: m/z 369.2 [M+1]$^+$; calc. M$^+$: 368.2.

Conjugation of 1 to quantum dots: Quantum dots, HaloTag ligand 1, and EDC (400 equiv.) were mixed together in borate buffer (10 mM, pH 7.4) and incubated at room temperature for 1 hour. QD@1 was separated from free HaloTag ligand and excess EDC by filtration through a 100K NanoSep filter. The quantum dot conjugates were washed 3 times with pH 8.5 borate buffer for 1 hr before recovered with pH 7.4 borate buffer. The concentration of QD@1 was determined from the fluorescence intensity.

Preparation and purification of HTP-Luc8: the plasmid pBAD-Luc8-HaloTag encoded for the fusion protein was constructed from plasmid pBAD-RLuc8 and plasmid pHT2 by PCR and ligation. *E. coli* LMG194 cells transformed with this plasmid were induced with 0.2% arabinose and grown at 32° C. to an OD$_{600}$ of 0.7. Cells were lysed by thawing in wash buffer (WB: 300 mM NaCl, 20 mM HEPES, 20 mM imidazole, pH 8) containing 1 mg/ml lysozyme, 10 µg/ml RNAse A, and 5 µg/ml DNAse I. Lysates were clarified by centrifugation and allowed to bind to nickel affinity resin (Ni-NTA Superflow, Qiagen) for 1 h at 4° C. with gentle mixing. After washing with WB, protein was eluted with elution buffer (300 mM NaCl, 20 mM HEPES, 250 mM imidazole, pH 8), further purified by anion exchange chromatography (Source 15Q resin, GE/Amersham), and followed by gel filtration chromatography with borate buffer.

Conjugation of QD@1 with HTP-Luc8: Typically 5 pmol of QD@1 was incubated with 20 equiv. of HTP-Luc8 in borate buffer (pH 7.4, 10 mM) at 37° C. for 30 m. Free HTP-Luc8 was removed from the incubation mixture by filtration through a 100K NanoSep filter at 4° C. The filtered conjugates were washed efficiently with pH 7.4 borate buffer at 4° C. The final quantum dot conjugates were recovered with ice cold pH 7.4 borate buffer.

Fluorescence and bioluminescence spectra were collected with a Fluoro Max-3 (Jobin Yvon Inc.). Bioluminescence spectra were acquired with excitation light blocked.

Example 2

Introduction

Fluorescent semiconductor quantum dots (QDs) have held exciting potential for molecular imaging in living biological samples since their initial development; however, all existing QDs require excitation from external illumination sources in order to fluoresce, which limits their application in imaging of living opaque subjects due to the resultant strong autofluorescence background and a paucity of excitation light at non-superficial locations. This example presents a new type of QD conjugates that can luminesce not by external illumination but via bioluminescence resonance energy transfer (BRET). These bioluminescent QD conjugates were prepared by coupling carboxylate-presenting QDs to a mutant of the bioluminescent protein *Renilla* luciferase, and were shown to emit long-wavelength (from red to near-infrared) bioluminescent light. This example demonstrates that bioluminescent QD conjugates can be imaged in living cells and in living animals, even in deep tissues, and are suitable for multiplex in vivo bioluminescence imaging. Availability of these bioluminescent QD conjugates will enable many new possibilities for imaging biological events in living subjects.

Much of the excitement towards QDs arises from their unique optical properties as fluorescence imaging probes in comparison to traditional organic fluorophores, such as high quantum yield, high molar extinction coefficients, narrow emission spectra, size-dependent tunable emission, and high photostability, all of which make QDs appealing for in vivo imaging. QDs fabricated with various coating molecules and functionalized with biomolecules such as small peptides, proteins, antibodies, and nucleic acids, have been applied in a number of imaging studies. All reported QDs, however, need excitation from external illumination sources in order to fluoresce, which often presents an inherent challenge in imaging opaque subjects such as small living animals. In biological tissues, there are ubiquitous endogenous chromophores such as collagens, porphyrins, and flavins, which are also excited and lead to significant background autofluorescence. In addition, short-wavelength excitation photons are largely absorbed in tissues, therefore, little light reaches and excites QDs present at non-superficial locations. To avoid these problems, ideal QDs would emit light with no need for excitation from external illumination sources. Such QDs would be more applicable for molecular imaging in small living subjects.

Discussion

Figure 8:
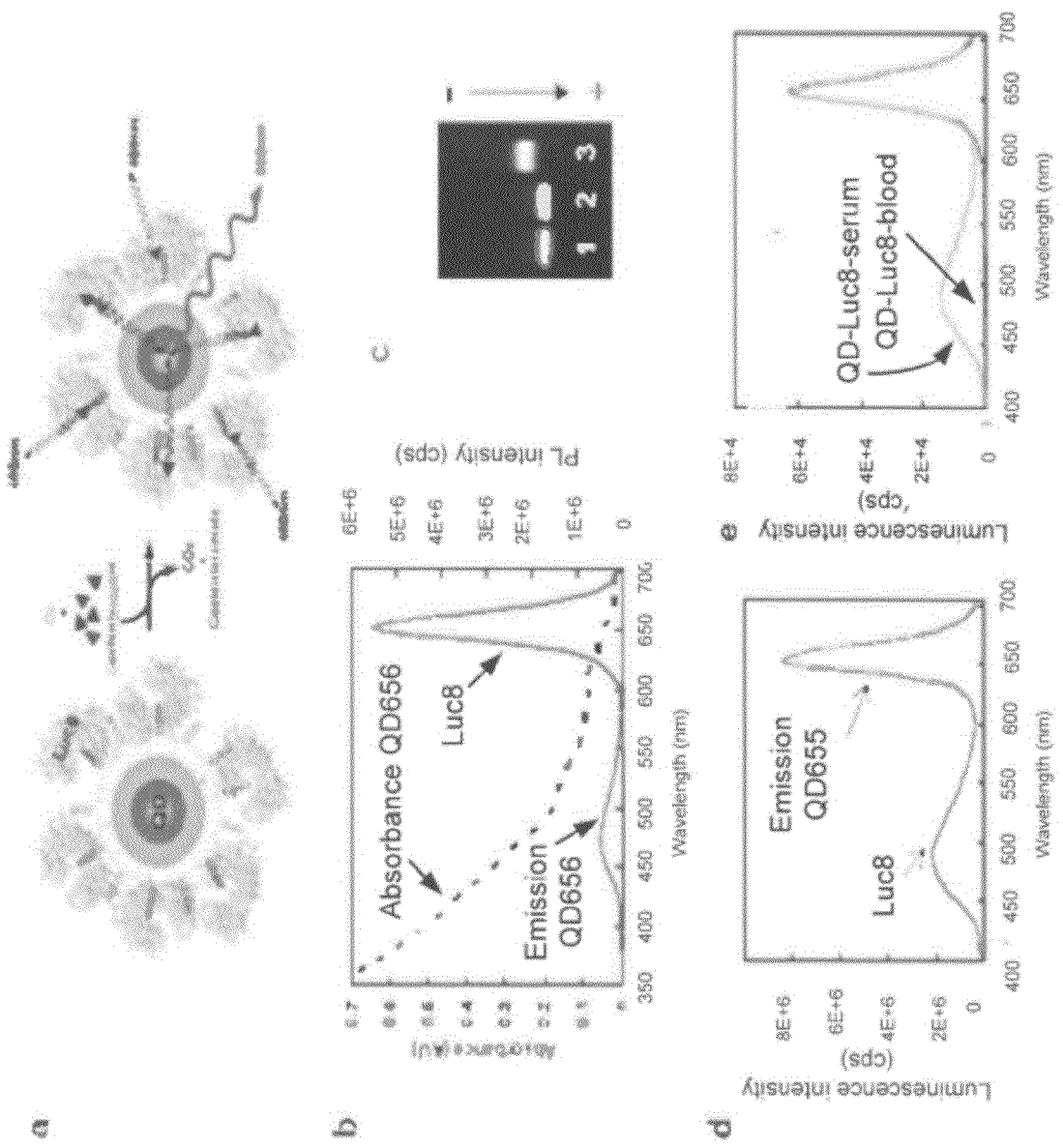
FIG. 8 illustrates the design and spectroscopic characterization of self-illuminating QD conjugates based on BRET.

This example describes a design for QD conjugates that can luminesce without external illumination sources based on the principle of bioluminescence resonance energy transfer (BRET). BRET is a naturally occurring phenomenon where a light emitting protein (the donor) non-radiatively transfers energy to a fluorescent protein (the acceptor) in close proximity. For example, in the sea pansy *Renilla reniformis*, the energy generated in the luciferase-catalyzed oxidation of the substrate coelenterazine is transferred to a green fluorescent protein (GFP) and emitted as green wavelength photons. Replacing GFP with a QD, the bioluminescence energy of the luciferase-catalyzed reaction could be transferred to the QD, resulting in light emission from the QD (FIG. 8a). A number of recent studies have demonstrated that fluorescence resonance energy transfer (FRET) can take place between QDs and organic dyes, but it has not been documented whether bioluminescence energy can be transferred to QDs. Furthermore, all reported QD FRET examples have used QDs as the energy donor, and it has been argued that QDs cannot be FRET acceptors for organic fluorophores.

Luciferase-based in vivo bioluminescence imaging has become a popular and powerful imaging technique for the study of biology due to its extremely high sensitivity. There are two commonly used luciferases: firefly luciferase that catalyzes the oxidation of D-luciferin in the presence of oxygen, ATP, and $Mg^{2+}$, with a maximal emission around 560 nm, and *Renilla* luciferase that catalyzes the oxidation of coelenterazine, with a maximal emission around 480 nm. D-luciferin and coelenterazine are administrated via intravenous or intraperitoneal injections at low doses that have not yet demonstrated any significant perturbation or toxicity to the subject. For the designing of bioluminescent QD conjugates, *Renilla* luciferase is better suited as the BRET donor since QDs absorb blue light more efficiently than light at longer wavelengths (FIG. 8b). A mutant of *Renilla* luciferase (containing 8 mutations and thus designated as "Luc8") with high serum stability and improved catalytic efficiency has been developed as previously mentioned above. Addition of the substrate, coelenterazine, to Luc8 led to the emission of blue light peaked at 480 nm (FIG. 8b). Luc8 was conjugated to polymer-coated CdSe/ZnS core-shell QD655 (with fluorescence emission at 655 nm) through amide coupling of the amino groups on Luc8 to carboxylates presented on the surface of the QDs. Gel electrophoresis analysis indicated altered mobility for the QD655-Luc8 conjugate compared to the unconjugated QD655, confirming successful conjugation (FIG. 8c). The hydrodynamic diameter of QD655-Luc8 conjugates, measured by quasi-elastic light scattering, was increased by approximately 2 nm in comparison to QD655. Each QD655-Luc8 conjugate was estimated to contain on average six copies of Luc8.

The bioluminescence emission of the QD655-Luc8 conjugate was examined upon the addition of coelenterazine (FIG. 8d). In addition to the bioluminescence emission of Luc8 at 480 nm, a strong new emission peak at 655 nm was detected, which is consistent with BRET occurring in our conjugate. The BRET ratio is determined by dividing the acceptor emission by the donor emission, and was 1.29 for our QD655-Luc8 conjugate (corresponding to an efficiency of 56%). For one mole of QD655-Luc8, the maximal blue photon emission (at 480 nm from Luc8) is $3.0 \times 10^{22}$ photons/s, and the maximal QD655 emission is $3.6 \times 10^{22}$ photons/s. In contrast, one mole of Luc8 in the borate buffer produces $1.5 \times 10^{22}$ photons per second under saturating concentrations of coelenterazine.

Figure 12:
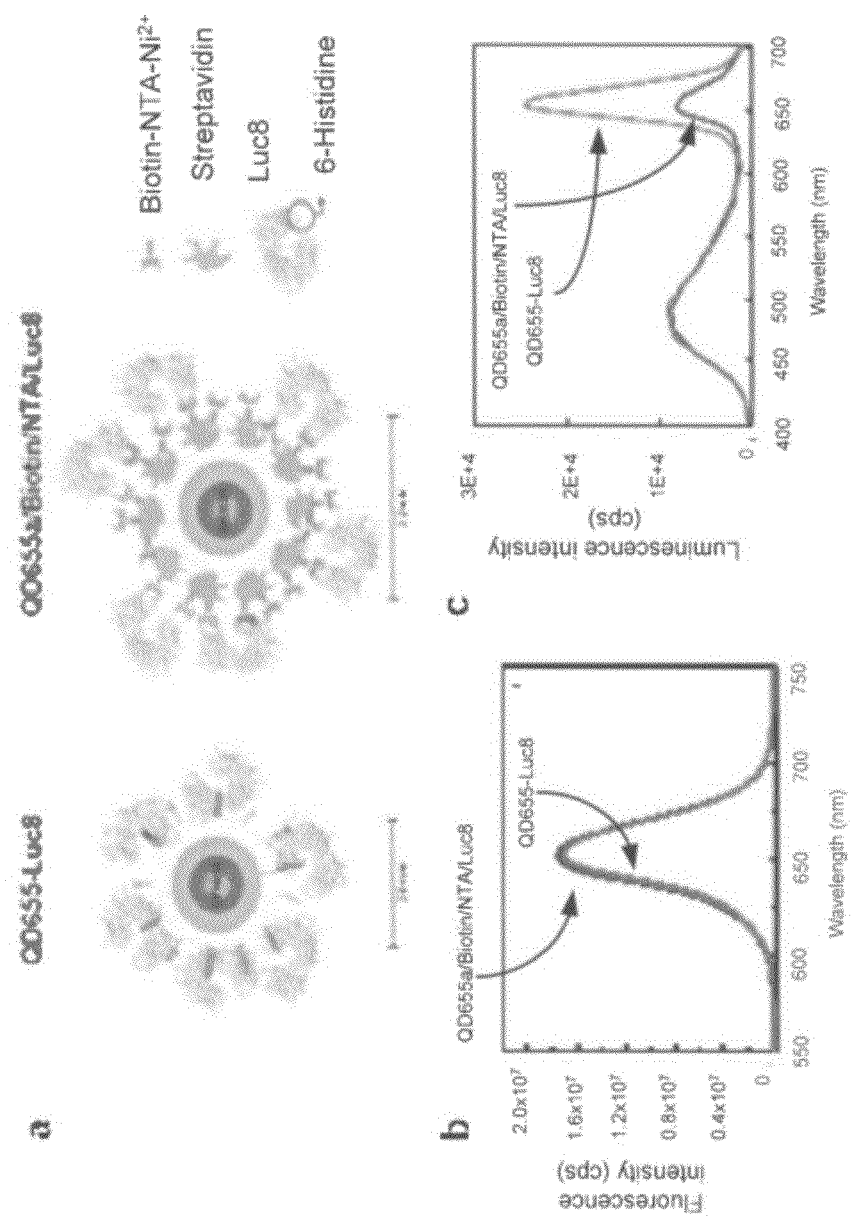
FIG. 12 illustrates the dependence of the BRET efficiency on the distance between QDs and Luc8's.
Figure 13:
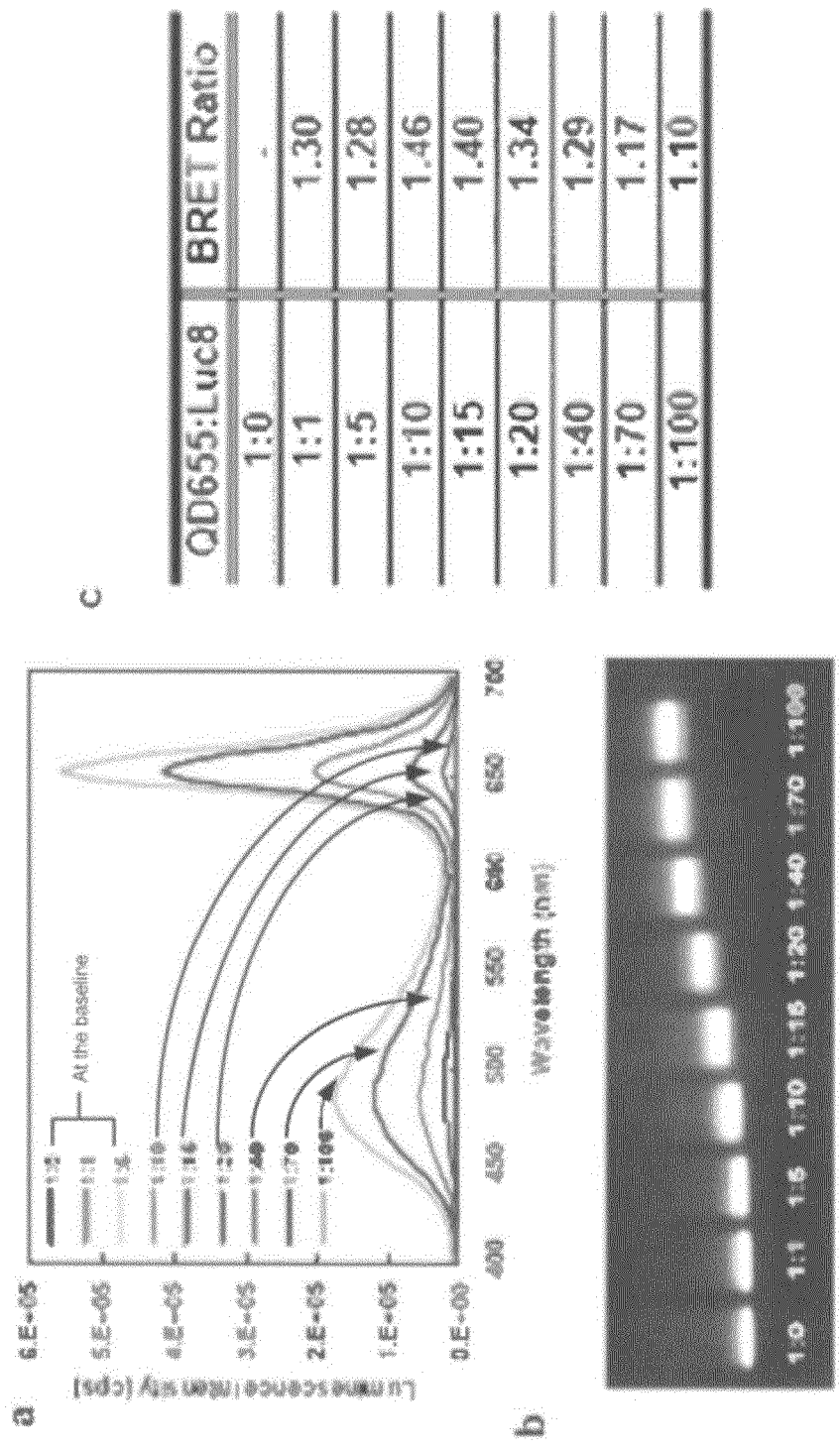
FIG. 13 illustrates the effect of the number of immobilized Luc8 on the BRET efficiency of QD655-Luc8 conjugates.

The BRET ratio was dependent on the distance between Luc8 and QD655. When the mean distance between Luc8 and QD655 was increased by approximately 2-3 nm, the BRET ratio dropped to ~0.37 (FIG. 12). When the ratio of QD655 to Luc8 in the coupling reaction was varied to make conjugates with varying numbers of Luc8, the BRET ratio among these conjugates was surprisingly similar, ranging from 1.10 to 1.46, although the intensity of both Luc8 and QD emission varied significantly (FIG. 13). In QD FRET examples where QDs serve as the donor, the FRET efficiency increased with increasing numbers of the FRET acceptor per QD. In contrast, the measured BRET efficiency in this QD-Luc8 conjugate is not the sum but the average of the resonance energy transfer efficiency from each individual Luc8 to the QD.

Figure 9:
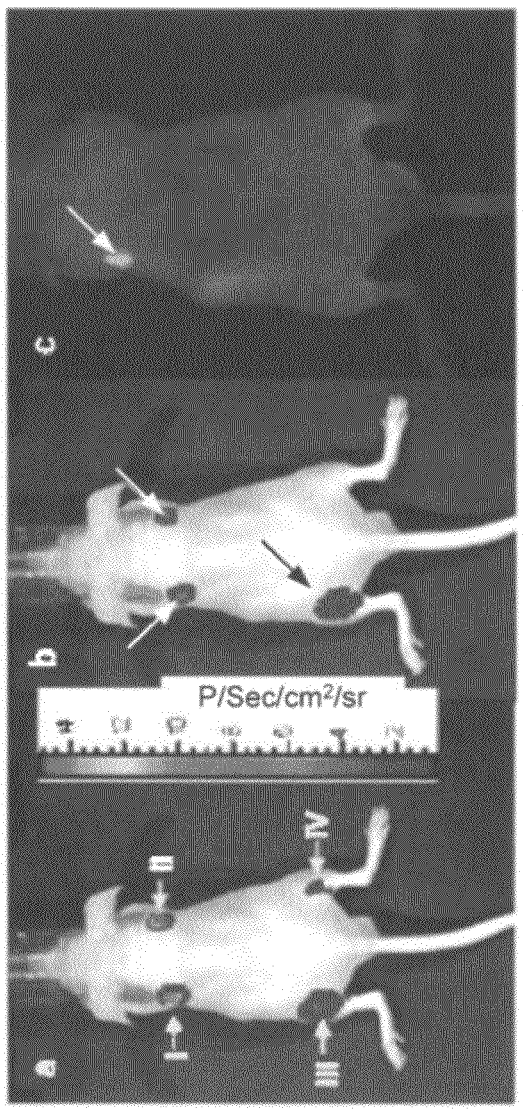
FIG. 9 illustrates the bioluminescence and fluorescence imaging of QD655-Luc8 and Luc8 injected subcutaneously (I and II) and intramuscularly (III and IV) at indicated sites in a living mouse (I and III: QD655-Luc8, 5 pmol; II and IV: Luc8, 30 pmol)
Figure 14:
FIG. 14 illustrates bioluminescence and fluorescence imaging of QD655-Luc8 and Luc8 injected subcutaneously (I and II) and intramuscularly (III and IV) at indicated sites in a living mouse (I and III: QD655-Luc8, 5 pmol; II and IV: Luc8, 30 pmol).

To assess whether BRET emission can be detected in living subjects, the emission of QD655-Luc8 (5 pmol) in mouse serum and whole blood was first examined. While the Luc8 emission nearly disappeared in whole blood because of absorption by hemoglobin, the BRET emission was not effected (FIG. 8e). A solution of QD655-Luc8 (5 pmol) was subcutaneously injected into the left shoulder of a nude mouse (injection site I in FIG. 9a). As a comparison, in the same mouse, a solution of Luc8 (30 pmol) was similarly injected into the right shoulder (II in FIG. 9a). Coelenterazine (10 μg) was subsequently injected via tail-vein, and the mouse was imaged sequentially: without any emission filter (so the emission from both Luc8 and QD655 was collected; FIG. 9a) and with an emission filter (575-650 nm, to collect the QD655 emission; FIG. 9b). Images collected without any emission filter showed strong emission intensities from both injection sites (FIG. 9a). The total photon fluxes from both sites were similar, indicating that the total activity of Luc8 was approximately the same at both sites. With the filter, there was still a strong signal from site I (left shoulder, QD655-Luc8, FIG. 9b), which was 60% of the intensity collected without the filter. However, the signal from Luc8 (right shoulder, FIG. 9b) was just 25% of that collected without the filter. When a narrow filter (650-660 nm) was used for the collection of only the BRET emission, there was an even lower amount of signal detected from site II (Luc8 injected in the right shoulder) while site I (QD655-Luc8 injected in the left shoulder) still emitted strongly (FIG. 14). These results indicate that BRET occurs between Luc8 and QDs and is detectable in living subjects at superficial depths.

The detection of the BRET emission of QD655-Luc8 was compared to the Luc8 emission in deeper tissues. A solution of QD655-Luc8 (5 pmol) was injected intramuscularly (at the depth of about 3 mm; injection III in FIG. 9a). As a comparison, a solution of Luc8 (30 pmol) was similarly injected into the same nude mouse (injection IV in FIG. 9a). In contrast to the subcutaneous injections (injections I and II in FIG. 9a), even without any filter, the emission of intramuscularly injected Luc8 was much weaker than QD655-Luc8 (IV vs III in FIG. 9a): the total detected photons from site IV was only 26% of that from site III. With the filter (575-650 nm), there was little detectable signal from the injected Luc8 but still a strong signal from the QD655-Luc8 conjugate (FIG. 9b). The bioluminescence intensity of the injected QD655-Luc8 imaged with the filter was 75% of the intensity without the filter. The increased ratio of detected QD655 emission versus Luc8 emission is due to preferential absorption of the shorter wavelength light (Luc8 emission) in tissues. Therefore, in deep tissues, the longer wavelength BRET emission of QD655-Luc8 is more readily detected than the short wavelength emission from Luc8.

The same mouse was examined with fluorescence spectral imaging for QD emission at sites where QD655-Luc8 was injected. A strong signal was observed from subcutaneously injected QD655-Luc8 (site I), but intramuscularly injected QD655-Luc8 (site III) emitted little signal (FIG. 9c). This result demonstrates the advantage of bioluminescence detection of signals from deep tissues with bioluminescent QD conjugates.

Figure 10:
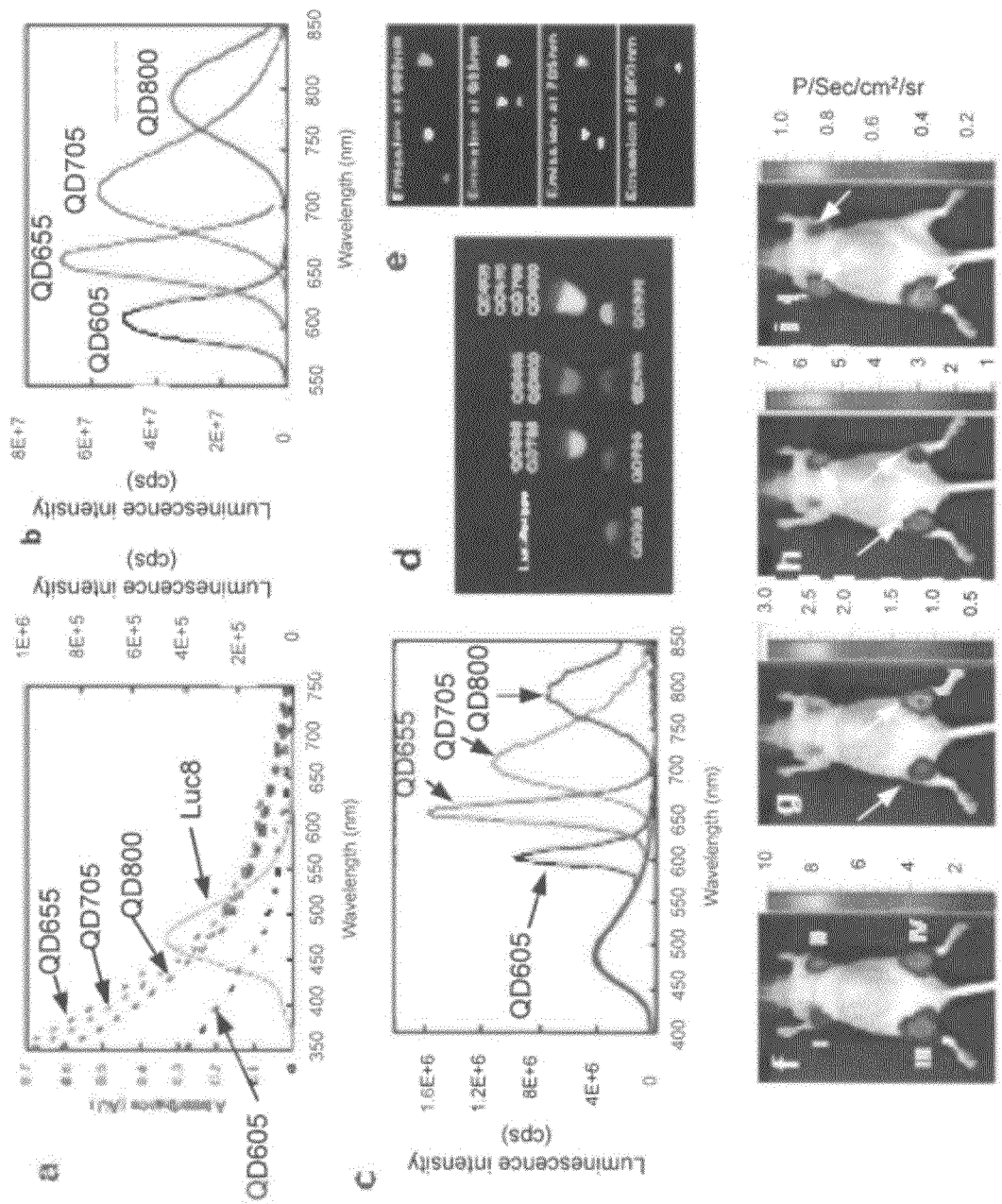
FIG. 10 illustrates multiplex imaging of conjugates QD605-Luc8, QD655-Luc8, QD705-Luc8, and QD800-Luc8 in vitro and in living mice.

One long-sought feature for in vivo bioluminescence imaging is to have a number of probes with distinct long-wavelength emissions to enable multiple target imaging. Since QDs have similar absorption spectra and all absorb blue wavelength light efficiently, Luc8 can serve as the BRET donor for other QDs than QD655 (FIG. 10a). Conjugates QD705-Luc8, QD800-Luc8, and QD605-Luc8 were similarly prepared. FIG. 10b displays the fluorescence emission spectrum of each QD conjugate, while FIG. 10c shows the bioluminescence spectrum of each QD conjugate upon the addition of coelenterazine. Clearly, BRET occurs in each conjugate. The BRET ratio of each conjugate is estimated as 0.70 for QD605-Luc8, 1.20 for QD655-Luc8, 2.30 for QD705-Luc8, and 1.32 for QD800-Luc8. This trend correlates well with the excitability of each QD (Example 2, Table 1). For example, QD705 and QD800 have the same extinction coefficient (1,700,000 M$^{-1}$ cm$^{-1}$ at 550 nm), but the quantum yield of QD705 is 80% and only 43% for QD800, hence the BRET ratio of QD800-Luc8 is just about half of QD705-Luc8.

TABLE 1

The BRET ratio of QD-Luc8 conjugates.

| QD-Luc8 | Quantum Yield [a] | Extinction Coefficient (M$^{-1}$cm$^{-1}$) [a] | BRET Ratio |
|---|---|---|---|
| QD605 | 65% | 650,000 (at 596-604 nm) | 0.70 |
| QD655 | 83% | 800,000 (at 638 nm) | 1.20-1.29 |
| QD705 | 80% | 1,700,000 (at 550 nm) | 2.30 |
| QD800 | 43% | 1,700,000 (at 550 nm) | 1.32 |

[a] Product specifications from Quantum Dot Corporation (Hayward, California).

The spectrally distinct emissions from the four QD conjugates make multiplex bioluminescence imaging feasible. This possibility was examined by first imaging solutions containing QD605-Luc8, QD655-Luc8, QD705-Luc8, QD800-Luc8, and their mixtures in vitro (FIG. 10d-e). Using bioluminescence spectral imaging, which is analogous to fluorescence spectral imaging but without excitation light, the bioluminescence emission from each conjugate could be selectively distinguished from the emissions of the other conjugates when it was either alone or mixed with the other conjugates.

QD655-Luc8 (5 pmol), QD705-Luc8 (15 pmol), QD800-Luc8 (15 pmol), and a mixture of all three conjugates were injected intramuscularly at four different sites on a nude mouse. After tail-vein injection of coelenterazine, the mouse was imaged for the bioluminescence emission from the conjugates. The total emission (from both Luc8 and BRET) was collected without any filter (FIG. 10f), and the BRET emission of each conjugate was collected with appropriate filters, for example, x-Cy5.5 filter for QD705-Luc8, and ICG filter for QD800-Luc8 (FIG. 10g-i). Similarly to the in vitro imaging data, all conjugates showed Luc8 emission, and each BRET emission was readily distinguished with appropriate filters, although there was a small degree of signal cross-talking due to the overlapping of the emission spectra between QD655-Luc8 and QD705-Luc8, and between QD705-Luc8 and QD800-Luc8 (FIG. 10b). With optimized filters ideal for QDs, the small degree of signal cross-talking can be prevented.

Figure 11:
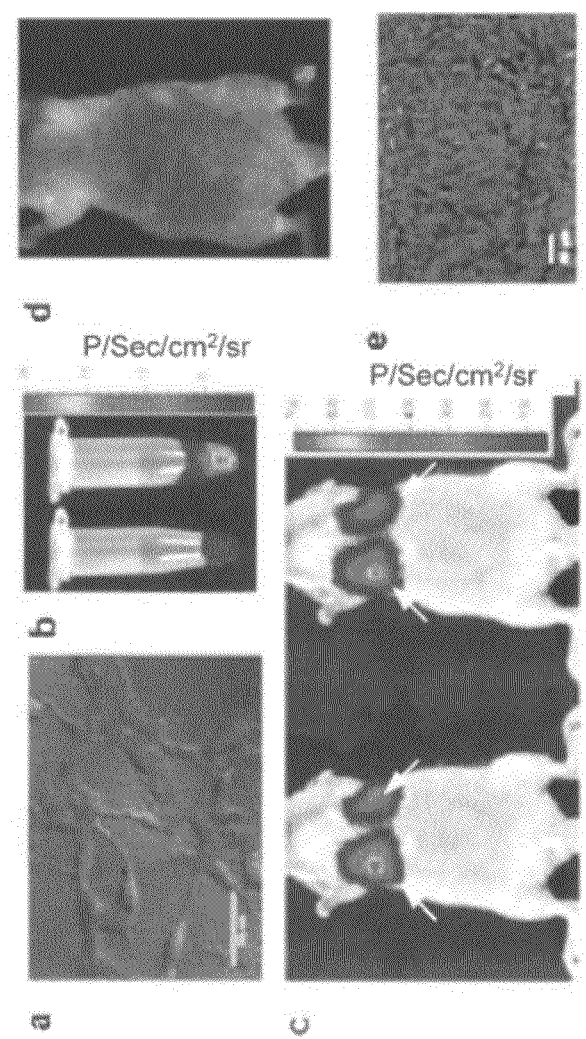
FIG. 11 illustrates the imaging of C6 glioma cells labeled with QD655-Luc8-R9 in vitro and in living mice.

Finally, the BRET conjugates were evaluated whether they could label living cells and monitor labeled cells in living animals. QD655-Luc8 by itself was able to enter living cells, but the uptake efficiency was improved when it was conjugated with a polycationic peptide such as an arginine 9-mer (QD655-Luc8-R9). The BRET ratio of QD655-Luc8-R9 was comparable to that of QD655-Luc8, indicating little impact on BRET from the additional conjugation of the arginine 9-mer. Cells incubated with QD655-Luc8-R9 for one hour at 37° C. displayed bright QD655 signals when observed under a fluorescence microscope (FIG. 11a). These cells were collected for assaying the luciferase activity, and upon the addition of coelenterazine, bright luminescence light was detected both in the absence and presence of the long wavelength filter (575-650 nm) (FIG. 11b). Without a filter, both the emissions from Luc8 and QD655 were detected (right tube in FIG. 11b); in the presence of the filter, the detected signal should mostly result from the BRET emission (left tube in FIG. 11b). The ratio of total emission from the left tube to that from the right tube was ~20%; this value is close to the ratio for emission collected with this filter, which is 18%, calculated from the emission spectrum of QD655-Luc8 (FIG. 8d). These results confirm that QD655-Luc8-R9 conjugates are functional and produce BRET emission after being taken up into cells.

The QD655-Luc8-R9 labeled cells (~2×10$^6$) were injected via the tail vein into a nude mouse. After subsequent i.v. injection of coelenterazine, the mouse was imaged with and without the long wavelength filter to examine whether BRET signals from these labeled cells could be detected in living mice. The left image in FIG. 11c, collected with the long-wavelength filter, showed injected cells located in both lungs of the mouse. The right image in FIG. 11c was collected without a filter. The total intensity is approximately the same in both images, suggesting that the Luc8 emission was significantly scattered and absorbed in deep tissues. A control mouse injected with unlabeled cells did not produce any detectable bioluminescence emission (data not shown).

For comparison, fluorescence spectral imaging of the same mouse was performed: only background fluorescence was observed, with no detectable QD fluorescence emission arising from the lungs (FIG. 11d). Epifluorescence microscopic examination of slices of the sacrificed mouse confirmed the presence of QD655-Luc8 conjugate in the lungs (FIG. 11e). The detection of labeled cells by in vivo bioluminescence QD imaging but not by fluorescence imaging further demonstrates the advantage of eliminating the need for external excitation and the power of bioluminescent QDs for imaging studies in living subjects. Fluorescence imaging of QDs requires light to travel in to excite the QDs, and emitted photons to travel out. With bioluminescent QDs, however, no external excitation light is required to travel in to the QDs. By eliminating the need for the excitation light, the surface weighting that occurs with traditional reflectance fluorescence imaging systems is removed, and the issue of background autofluorescence, a major limiting complication for in vivo fluorescence imaging, is completely avoided.

One of the challenges for the use of QDs as in vivo targeting agents is the relatively large size of these particles. The bioluminescent QD conjugates contain, on average, six copies of immobilized Luc8 with the overall size of around 20 nm. Surface coating of QDs with high molecular weight polyethylene glycol (PEG) chains has been shown to extend the circulation time and improve their bioavailability. Further modifications of QD-Luc8 conjugates with PEG should further facilitate their in vivo tumor targeting.

In summary, this example describes the first example of bioluminescent QD conjugates designed by mimicking the natural BRET process, using a mutant of *Renilla* luciferase as the energy donor and a QD as the acceptor. This example demonstrates that the long wavelength BRET emission can be imaged in both living cells and small living animals. There are several unique features with this system: 1) both bioluminescence and fluorescence imaging can be performed with our bioluminescent QDs, combining advantages of both imaging techniques. While conserving the optical properties of QDs, bioluminescent QDs offer an additional advantage over existing QDs: the ability to be imaged without external excitation (bioluminescently) results in greatly enhanced sensitivity in the context of small animal imaging. 2) Bioluminescence emission at longer wavelengths (from 655 nm to near-infrared 800 nm) than any current bioluminescence probe is readily available by choosing appropriate QDs. These long wavelength emissions are more easily detected, especially in deep tissues. 3) In vivo multiplexed bioluminescence imaging of multiple targets can be performed by using multiple QD conjugates with distinct BRET emission spectra. These unique features of bioluminescent QD probes should open many new avenues for QD-based imaging, including bioluminescence-based, highly sensitive in vitro assays of multiple targets, cell labeling, in vivo cell trafficking, tumor imaging, in vivo multiplexed imaging, and even the design of QD-based biosensors where the BRET emission is modulated by specific biological interactions of interest.

Materials and Methods

Materials: Quantum dots were purchased from Quantum Dot Corp. (Hayward, Calif.). QD605 and QD655 have typical CdSe/ZnS core-shell structures, and QD705 and QD800 are made of CdTe cores with ZnS coatings. The organic coating chemistry has been previously described in the literature, and the final coated QDs are endowed with carboxylate groups. The quantum yields of each QD determined in 50 mM borate buffer (pH 9) are 65% (QD605), 83% (QD655), 80% (QD705), and 43% (QD800). The hydrodynamic diameters of all QDs and conjugates were measured with a Zetasizer Nano ZS and performed by Malvern Instruments Ltd. (Southborough, Mass.). The coupling reagent 1-ethyl-3-(3-dimethylaminopropyl)carbodiimide hydrochloride (EDC) was obtained from Fluka. Coelenterazine, the substrate for Luc8, was purchased from Prolume (Pinetop, Ariz.). All other chemicals and solvents were from Sigma-Aldrich. Nude mice (4-6 weeks old) were purchased from Charles River Breeding Laboratories. Water was purified with Milli-Q biocel (Millipore Corp.). Fluorescence and bioluminescence emission spectra were collected with a Fluoro Max-3 (JOBIN YVON Inc., New Jersey); in the case of bioluminescence, the excitation light was blocked, and emission spectra were corrected with a correction file provided by the company. The bioluminescence emission spectra collected with the spectrofluorometer were further corrected for the Luc8 kinetics over the course of data acquisition (typically ~20 s). The enzymatic activity of Luc8 was measured with a 20/20" Luminometer (Turner Biosystems, Inc.). Animal fluorescence imaging was carried out with a Maestro imaging system (Cambridge Research & Instrumentation, Inc.). Animal bioluminescence imaging was performed with a Xenogen IVIS 200 (Xenogen Corp.). Animal use protocols were reviewed and approved by the Institutional Animal Care Use Committee of Stanford University.

Preparation of QD and Luc8 conjugates: To a mixture of 8.2 pmol of QD and 164 pmol of Luc8 (20 equivalents) in 200 µL borate buffer (pH=7.4) was added of 32.8 nmol of EDC (4,000 equivalents) (Borate buffer was chosen to minimize QD aggregation during the coupling). The mixture was incubated for 1 h, and the uncoupled free Luc8 and excess EDC were removed by 3 washes in 100K NanoSep filter (Pall Corporation, New York) by centrifugation at 5000 rpm for 3 min at 4° C. The final complex was kept in borate buffer (pH=7.4) at 4° C.

Gel electrophoresis: 1.0 pmol of QD655-Luc8 complex, QD655, and the reaction mixture of QD655 and EDC, with 6× loading dye was run on a 0.5% agarose gel at 100 V in TAE buffer (0.5×).

Cell labeling with QD-Luc8-R9: 8.2 pmol of QD655-Luc8 was activated by 1,000 1.64 nmol of EDC (1,000 equivalents) for 5 min. Then 1.64 nmol of peptide R9 (200 equivalents) was added, and the mixture was incubated for 30 min. The conjugated product was purified by washing and centrifugation. C6 rat glioma cells were cultured in Dulbecco's Modified Eagle Medium supplemented with 10% (vol/vol) fetal bovine serum (Gibco) and 1% antibiotic-antimycotic mixture (Gibco). Before incubation with QD conjugates, the culture media were replaced by Hank's Balanced Salt Solution (HBSS). After incubation with QD-Luc8-R9 (1 ml, 10 nM) at 37° C. for 1 h, cells were washed with HBSS 3 times and imaged with an inverted fluorescence microscope (Axiovert 200M, Zeiss). The following filter set (Chroma Technology Corporation) was used for QD655 analysis: excitation, 420/40; emission, D660/40; dichroic, 475DCXR. Acquisition time: 50 ms, and 40× magnification. For the bioluminescence imaging of labeled cells, cells were collected by trypsinization or cell scrapers, and suspended in 50 µL of HBSS. After addition of 2 µg of coelenterazine, cells were imaged immediately with an IVIS 200 bioluminescence imager with and without filter (30 s for each acquisition).

In vivo bioluminescence imaging: QD conjugates (or labeled cells) were injected either subcutaneously, intramuscularly or via tail-vein into nude mice. Mice were subsequently anesthesized with isofluorane, and transferred into the light-tight chamber of an IVIS 200 imager. After 10 min, coelenterazine (10 µg/mouse in 100 µL buffer) was injected i.v. The images were acquired with and without filters. Each single acquisition took 30 s (for injected QD conjugates) or 2 min (for labeled cells). To correct for the relatively fast in vivo pharmacokinetics of coelenterazine, the images were acquired sequentially: 1) with filter (30 s); 2) without filter (30 s); 3) without filter (30 s); 4) with filter (30 s). The emission with filter was calculated from the average of 1 and 4, and the emission without filter was the average of 2 and 3.

In vivo fluorescence imaging: Wavelength-resolved spectral imaging was carried out by using a spectral imaging system (Maestro™ In-Vivo Imaging System from Cambridge Research & Instrumentation, Inc. (CRi)) including an optical head that includes a liquid crystal tunable filter, an optical coupler, and a CCD camera, along with image acquisition and analysis software. Excitation filter was 503-555 nm. The tunable filter was automatically stepped in 10-nm increments from 580 to 900 nm with an exposure time of 49 ms for images captured at each wavelength. Animals were placed supine under isofluorane anesthesia in a light-tight chamber. Collected images were analyzed by the Maestro software, which uses spectral unmixing algorithms to remove autofluorescence from the QD signals. The in vitro multiplexing bioluminescence imaging of QD conjugates was performed similarly with the Maestro system, but with the excitation light blocked and 5 s exposure time for each individual acquisition.

Histology. Nude mice were sacrificed 1 h and 20 min after injection of QD-labeled cells. Lungs were collected, washed with PBS, frozen in isopropanol with liquid nitrogen, and kept at −80° C. over night. Frozen samples were microtome sectioned at a thickness of 10 µm. Slides were analyzed under a Zeiss inverted fluorescence microscope with the same QD filter set as described above (objective: 20×; acquisition time: 1 s).

Example 3

Discussion

Semiconductor quantum dots (QDs) are bright fluorescent emitters with high quantum yield, high molar extinction coefficients, size-dependent tunable emission, and high photostability. These attractive fluorescent properties prompt a wide interest in developing QD-based sensors for biological detection and imaging. One strategy towards the development of QD-based nanosensors is based on fluorescence resonance energy transfer (FRET) with the QDs as the FRET donor. There are numerous examples of FRET-based QD biosensors including self-assembled nanocomplexes for detecting maltose, pH, 2,4,6-trinitrotoluene, thrombin, and enzyme activity. In these FRET-based QD nanosenors, multiple copies of the FRET acceptor were often present on one QD, which may result in the self-quenching and lead to low emission from the FRET acceptor.

Matrix metalloproteinases (MMPs) are a family of zinc-dependent secreted endopeptidases crucial for regulated degradation and processing of extracellular matrices, and are upregulated in almost every type of human cancers. The significant role of MMPs in promoting cancer progression makes them important targets for drug development and in vivo tumor detection. Fluorescence and magnetic resonance-based approaches have been used to detect MMPs activity. This example describes a BRET-based QD nanosensor to detect the activity of gelatinase MMP-2 with high sensitivity.

Figure 15:
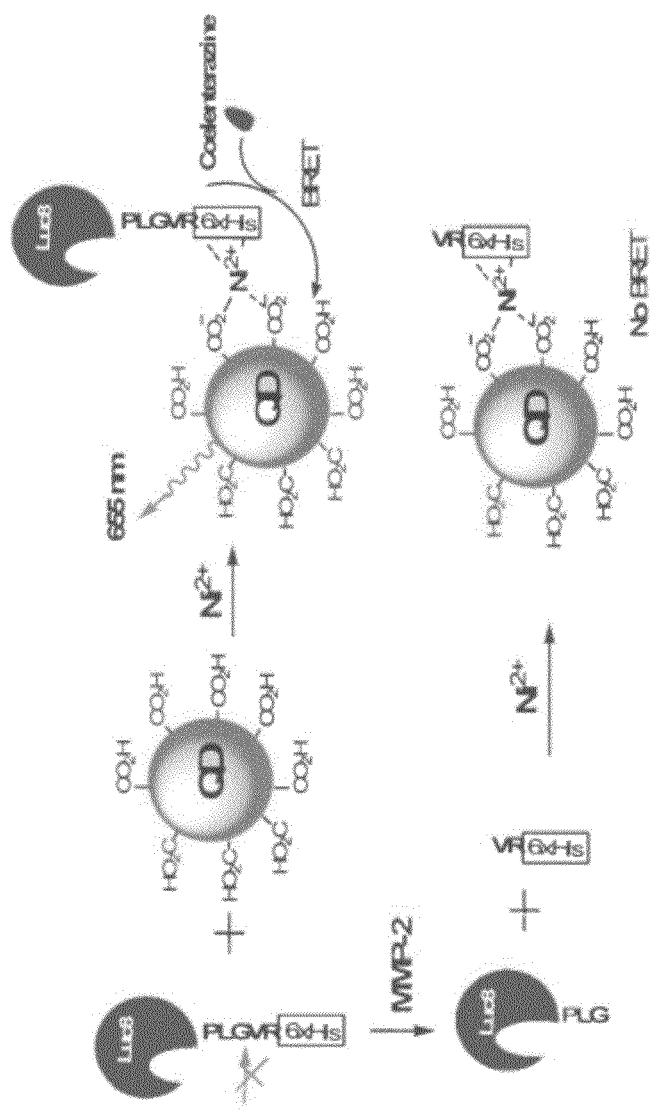
FIG. 15 illustrates a schematic for BRET-based detection of MMP-2 with Nanosensors.

The gelatinase MMP-2 has been identified as one of the key MMPs in degrading type-IV collagen. The design of a BRET-based QD sensor for the detection of the MMP-2 activity is shown in FIG. 15. MMP-2 hydrolyzes the peptide substrate containing an amino acid sequence of PLGVR. PLGVR can be fused to the C-terminus of the BRET donor, a mutant of *Renilla* luciferase (Luc8) without affecting the activity of Luc8. In addition, a 6xHis tag was added to the C terminus after PLGVR. In this example, commercially available QDs were used with carboxylic acids presented at the surface, QD@COOH. In the presence of $Ni^{2+}$, the carboxylic acids on the QDs will bind the metal ions and form complexes with the 6xHis tag on the Luc8 fusion protein (FIG. 15). The BRET will take place and produce light emission from the QDs. The cleavage of PLGVR by MMP-2 will release the 6xHis tag from the fusion Luc8 and disrupt the BRET (FIG. 15).

Figure 16:
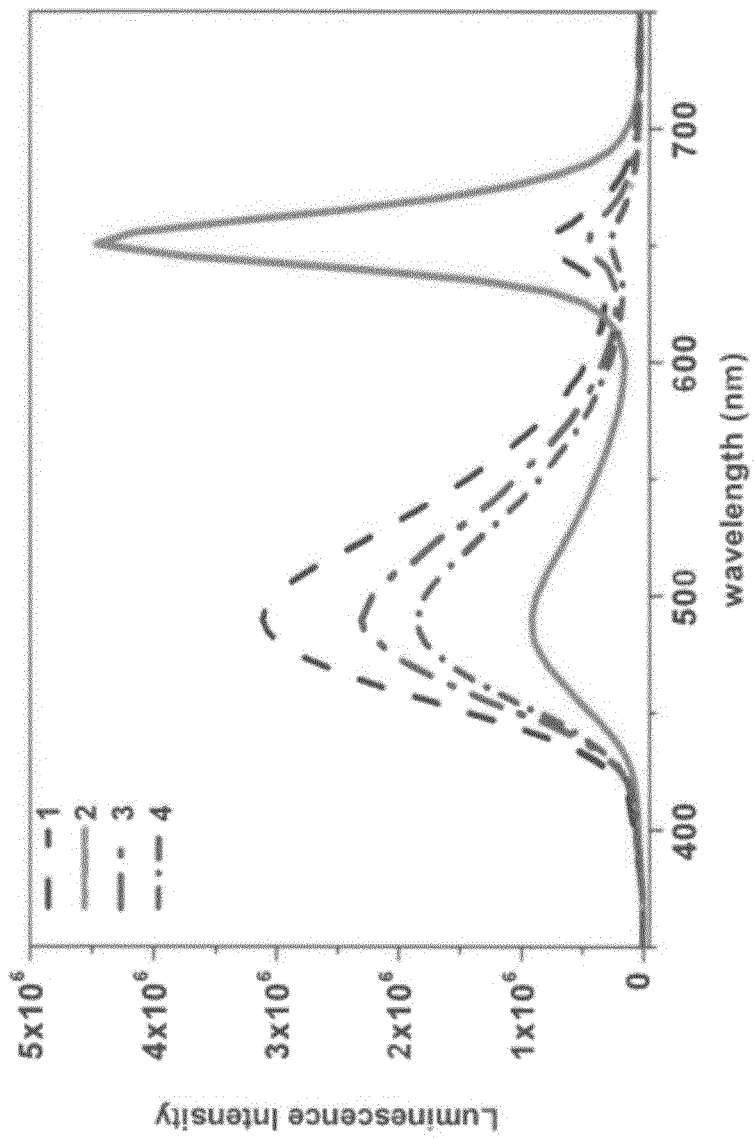
FIG. 16 is a luminescence spectra of the mixture of QD655@COOH (50 nM) and Luc8-6xHis fusion protein (400 nM) containing 1) No $Ni^{2+}$, 2) $Ni^{2+}$ (100 μM), 3) $Ni^{2+}$ (100 μM) and EDTA (200 μM), and 4) $Ni^{2+}$ (100 μM) and imidazole (300 mM).

The efficiency of the $Ni^{2+}$-induced BRET between the QDs and the Luc8 fusion protein was first evaluated. When QD655@COOH (50 nM) was mixed with the fusion protein (400 nM) in the absence of $Ni^{2+}$, upon the addition of the substrate of Luc8 coelenterazine (1 μg), there was a large emission from Luc8 at 480 nm but only a small emission from the QDs at 655 nm (<5% of the total emission from Luc8) (FIG. 16). This small peak at 655 nm likely arose from an electrostatic interaction between the 6xHis tag on the Luc8 and the negative carboxylate groups on the QDs. However, when $Ni^{2+}$ (100 μM) was added to the mixture, the emission at 480 nm decreased largely and the emission at 655 nm from the QDs increased significantly, indicating that BRET occurred efficiently between the QDs and Luc8. The BRET ratio, defined by the ratio of the integration of the peak at 655 nm to that of the peak at 480 nm, increased to 1.94.

Both the carboxylate groups on the QDs and the histidine tags on the Luc8 are used for the $Ni^{2+}$-mediated BRET. Addition of an excess amount of EDTA (200 μM), a strong chelator for $Ni^{2+}$, to the mixture containing QD@COOH, the fusion protein and $Ni^{2+}$ greatly decreased the BRET emission (FIG. 16). EDTA competed against the QD@COOH for $Ni^{2+}$ ions, leading to the dissociation of the QD@COOH and Luc8 complex and, consequently, disrupting the BRET process. When the QDs coated with amino groups (QD655@$NH_2$) replaced QD655@COOH, no BRET emission from the QDs was detected, further confirming that the carboxylate on the QDs are used for the binding of $Ni^{2+}$ and BRET. When imidazole was added to the mixture containing QD@COOH, the Luc8 fusion protein and $Ni^{2+}$, a large decrease in the BRET emission was observed; correspondingly, there was a large increase in the Luc8 emission at 480 nm (FIG. 16). These results indicate that the interaction between Luc8 and QD@COOH mediated by $Ni^{2+}$ is specific and dependent on the histidine tag.

Figure 17A:
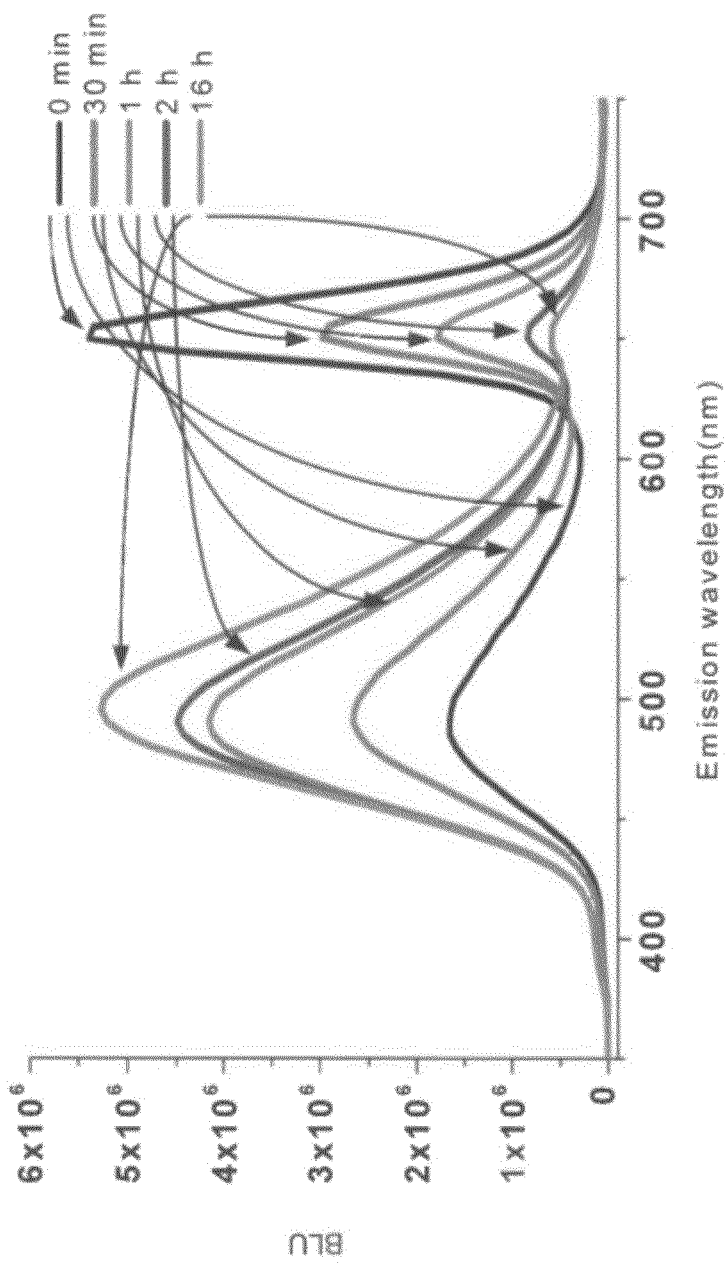
FIG. 17A illustrates a representative bioluminescence emission spectra of the mixture containing QD655@COOH (40 nM), $Ni^{2+}$ (100 μM), and the Luc8 fusion protein (16 μM) incubated with MMP-2 (10 μg/mL) at the indicated periods of time.
Figure 17B:
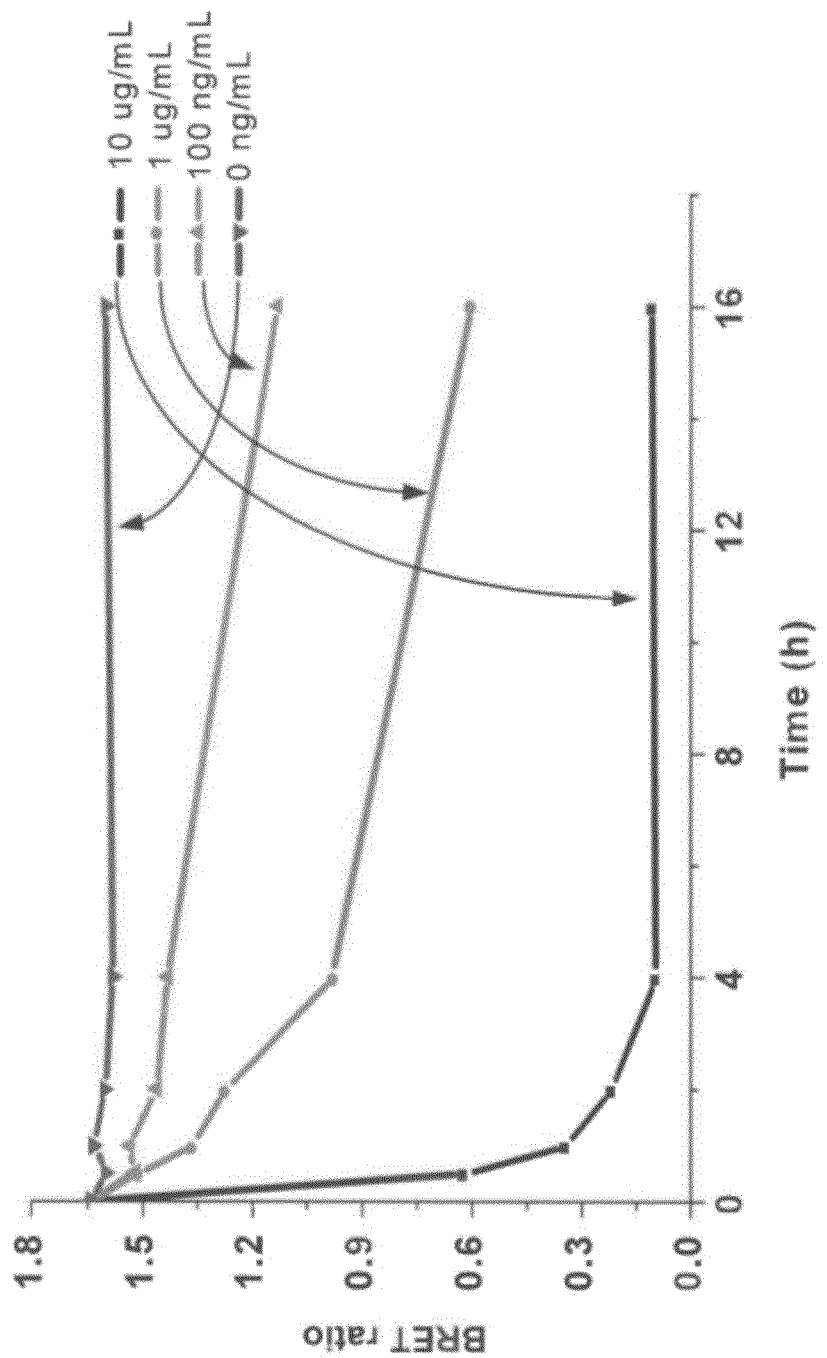
FIG. 17B illustrates a plot of the BRET ratio vs. time for indicated MMP-2 concentrations.

After establishing the $Ni^{2+}$-mediated BRET between the QDs and the Luc8 fusion protein, these results were applied to the detection of the protease MMP-2. MMP-2 hydrolyzes the amide bond between the glycine and valine residues, leading to the cleavage of 6xHis tag from the Luc8 fusion protein and the decrease in the BRET ratio. A solution of the Luc8 fusion protein (16 μM in the borate buffer) was incubated with MMP-2 (10 μg/mL) for various periods of time at 22° C., and then was added to a solution containing QD@COOH (40 nM) and 100 μM of $Ni^{2+}$ for the measurement of the BRET emission (FIG. 17). Before the MMP-2 cleavage (t=0), there was a strong emission from the QD655 at 655 nm, and the BRET ratio was 1.64. Within 30 minutes, the BRET ratio dropped to 0.62, and the reaction was nearly complete within 2 hours with a BRET ratio of 0.21. NuPAGE assay detected a protein product with a smaller size, confirming the hydrolysis by MMP-2.

The sensitivity of this assay was measured with various concentrations of MMP-2. After 24 hours of incubation at 22° C., the BRET ratio decreased by ~20% from 1.6 to 1.3 for a concentration of MMP-2 of 20 ng/mL (~300 pM). The BRET ratio for the control did not change at all. This sensitivity is much higher than reported FRET-based sensors and similar to the magnetic sensors.

In comparison to FRET-based QD sensors, BRET-based QD biosensors offer several advantages. The spectral separation between the BRET donor and acceptor emission is large, for example, the difference of the maximal emission wavelength in this example is more than 175 nm, which makes easy to detect both emissions. The sensitivity is high with low background emission. Because of the wide absorption spectra of the QDs, one bioluminescent protein such as *Renilla* luciferase can efficientlyxcite multiple QDs with different emissions. In the FRET-based QD sensors, several different FRET acceptors are required for multiple QDs with different emissions. Furthermore, the presence of multiple copies of the BRET donors on the QD does not decrease but increases the BRET emission.

In summary, the BRET-based QD biosensing system described here utilizes commercially available carboxylate QDs and a bioluminescent fusion protein containing a histidine tag and MMP-2 substrate to detect the protease MMP-2 activity with high sensitivity. This system is simple to use with no need for QD modifications. It offers several advantages over FRET-based sensing mechanism and may serve as a general strategy to design QD nanosensors for multiplex detection of biological analytes.

Materials and Methods

Preparation of the Luc8 Fusion Protein:

The plasmid Luc8-MMP2-pRSF-Duet was constructed from plasmid pBAD-RLuc8 by PCR and ligation, the MMP2 cleavage site, encoding the amino acid sequence PLGVR, was inserted between Luc8 and 6xHis tag. *E. Coli* BL21 cells transformed with this plasmid were induced with 0.5 mM IPTG for 3 hours when the optical density at a wavelength of 600 nm ($OD_{600}$) was 0.5. Cells were lysed by thawing in wash buffer solution (WB; 300 mM NaCl, 20 mM 2-[4-(2-hydroxyethyl)-1-piperazinyl]ethanesulfonic acid (HEPES), pH 8.0), containing lysozyme (1 mg/mL), RNase A (10 μg/mL), and DNaseI (5 μg/mL). Lysates were clarified by centrifugation and allowed to bind to nickel affinity resin (Ni-NTA superflow, Qiagen) for 1 h at 4° C. with gentle mixing. After washing with WB, the protein was eluted with elution buffer solution (300 mM NaCl, 20 mM HEPES, pH 8.0, 250 mM imidazole) and further purified by anion-exchange chromatography (Source 15Q resin, GE/Amersham) followed by gel-filtration chromatography with borate buffer solution.

Figure 18:
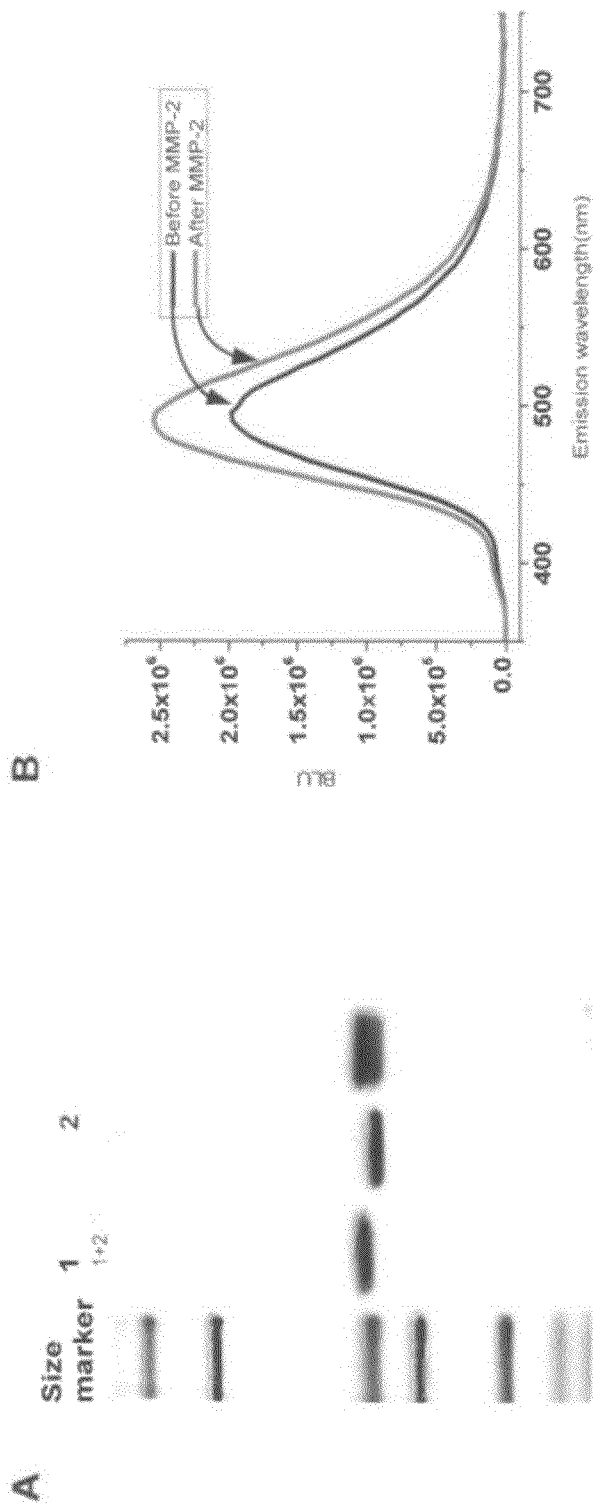
FIG. 18 illustrates MMP-2 cleavage of the Luc8 fusion protein.

MMP-2 Assay:

A solution of 5 μM of the Luc8 fusion protein in borate buffer (10 mM $CaCl_2$, pH 7.5) was incubated with various amounts of active human recombinant of MMP-2 (CalBiochem) for a period of time at room temperature. The BRET measurement was performed by mixing QD655@COOH (40 nM), protein (500 nM) and NiCl$_2$ (100 μM) in borate buffer (pH 7.5) with Fluoro Max-3 (Jobin Yvon Inc.). Bioluminescence spectra were acquired with the excitation light blocked. Gel electrophoresis analysis confirmed the cleavage of the fusion protein by MMP-2. Proteins were run on a 4-12% Bis-Tris gradient denaturing gel and stained with commassie blue (FIG. 18).

Figure 19:
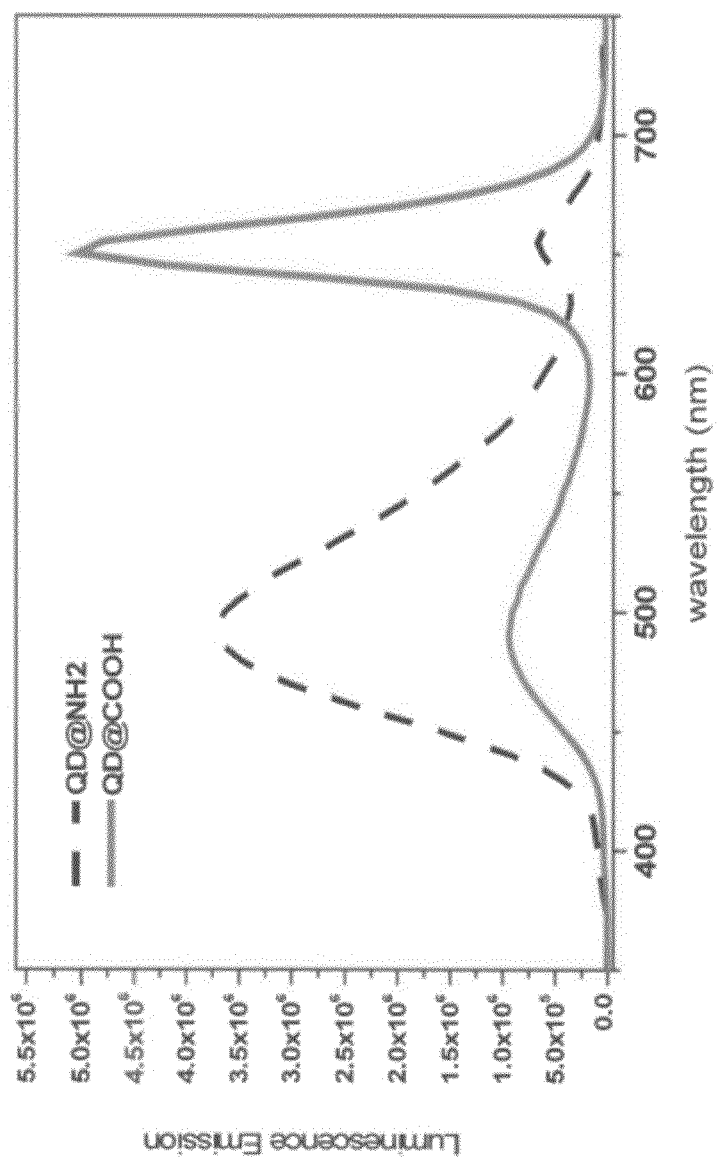
FIG. 19 illustrates the luminescence spectra of QD655@COOH (solid line) and QD655@NH$_2$ (dashed line) in the presence of 100 μM of $Ni^{2+}$ and 400 nM of Luc8 fusion protein.

Comparison of Carboxylate QDs and Amino QDs for Ni$^{2+}$-Mediated BRET:

The carboxylates on QDs are important for the Ni$^{2+}$-mediated BRET. When the QDs coated with amino groups (QD655@NH$_2$) replaced QD655@COOH, little BRET emission from the QDs was detected, further confirming that the carboxylate groups on the QDs are critical for the binding of Ni$^{2+}$ and BRET (FIG. 19).

Figure 20:
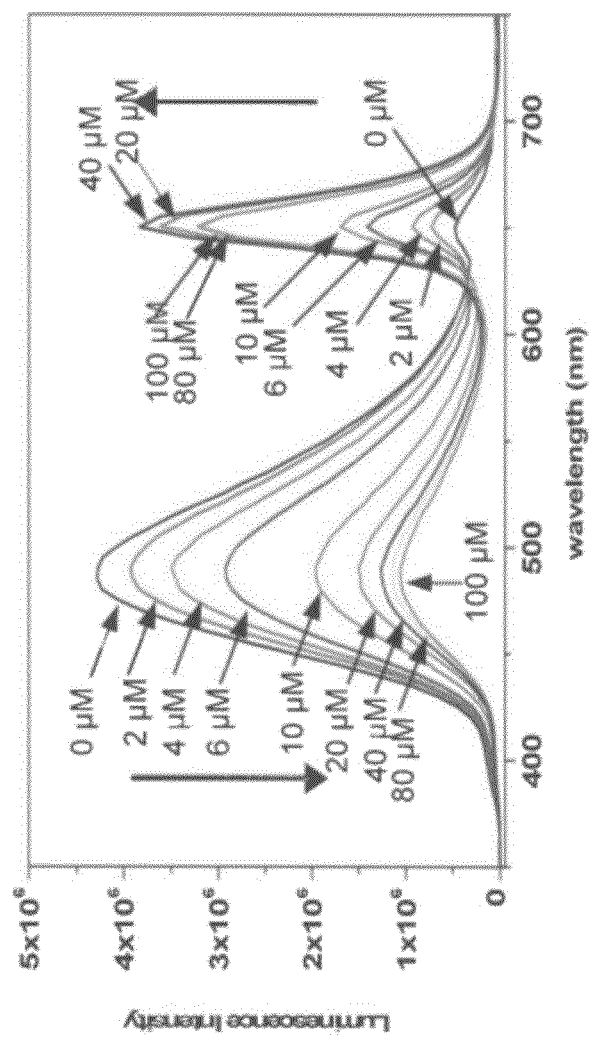
FIG. 20 illustrates the dependence of the BRET emission on the [$Ni^{2+}$] with representative bioluminescence spectra of the mixture containing QD655@COOH (20 nM), the fusion protein (640 nM) and different concentrations of $Ni^{2+}$ (0, 2, 4, 6, 10, 20, 40, 80, and 100 μM).

Dependence of the BRET Emission on [Ni$^{2+}$]:

The BRET emission is dependent on the concentration of Ni$^{2+}$. As shown in FIG. 20, with the increase in the concentration of [Ni$^{2+}$] from 0 to 40 μM, the BRET signal from QD kept increasing. Further increase in [Ni$^{2+}$] did not result in an increase in the BRET ratio, indicating all the QD surface binding sites have been saturated with the Luc8 fusion protein. Thus in all of our BRET measurements, 100 μM of [Ni$^{2+}$] was used to ensure the complex formation.

Example 4

Quantum Dot Probes for Multiplexed High Throughput Kinase Activity Assay

Figure 21:
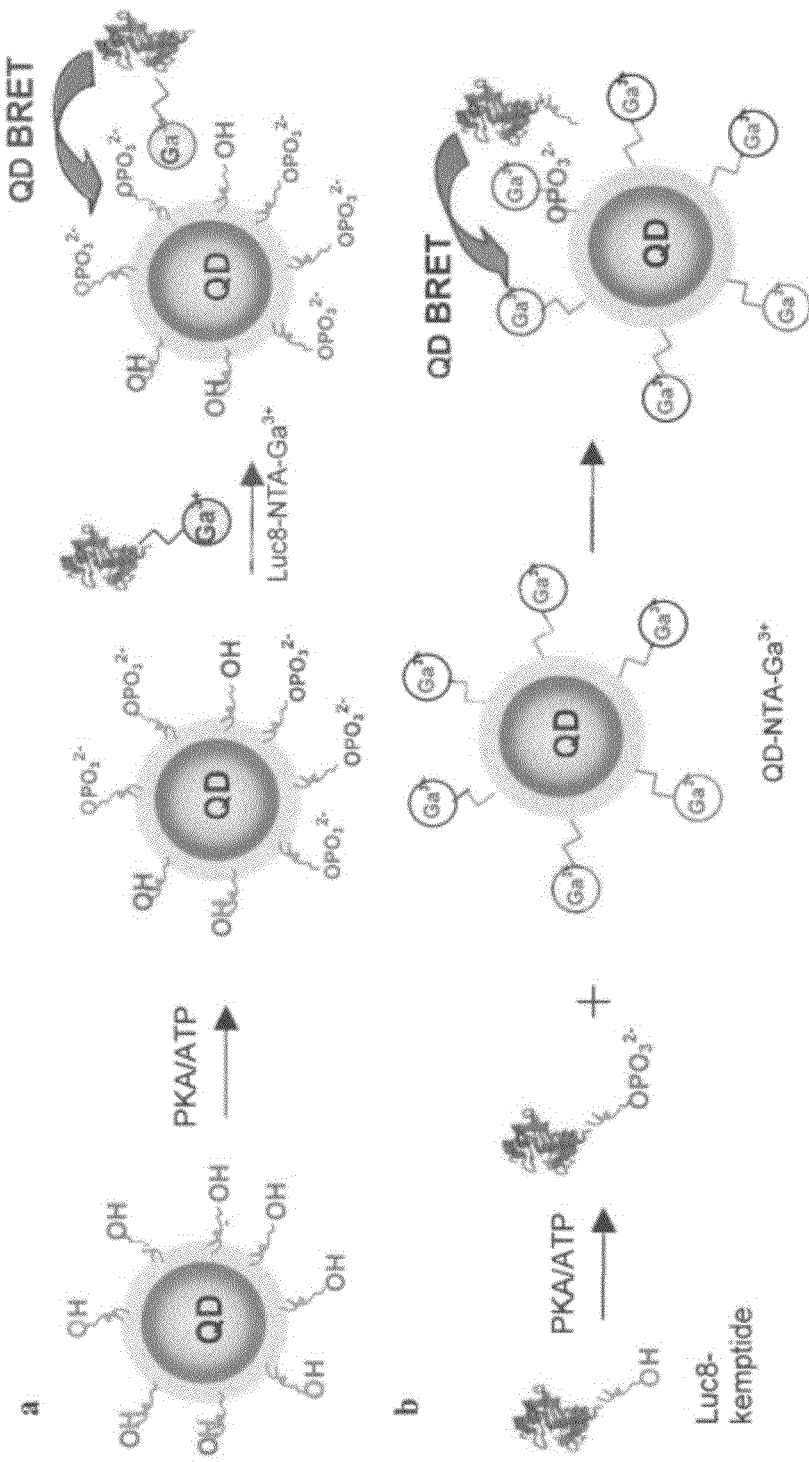
FIG. 21 illustrates a schematic of the PKA detection based on the formation of the self-Illuminating complex mediated by the PKA phosphorylation.
Figure 22:
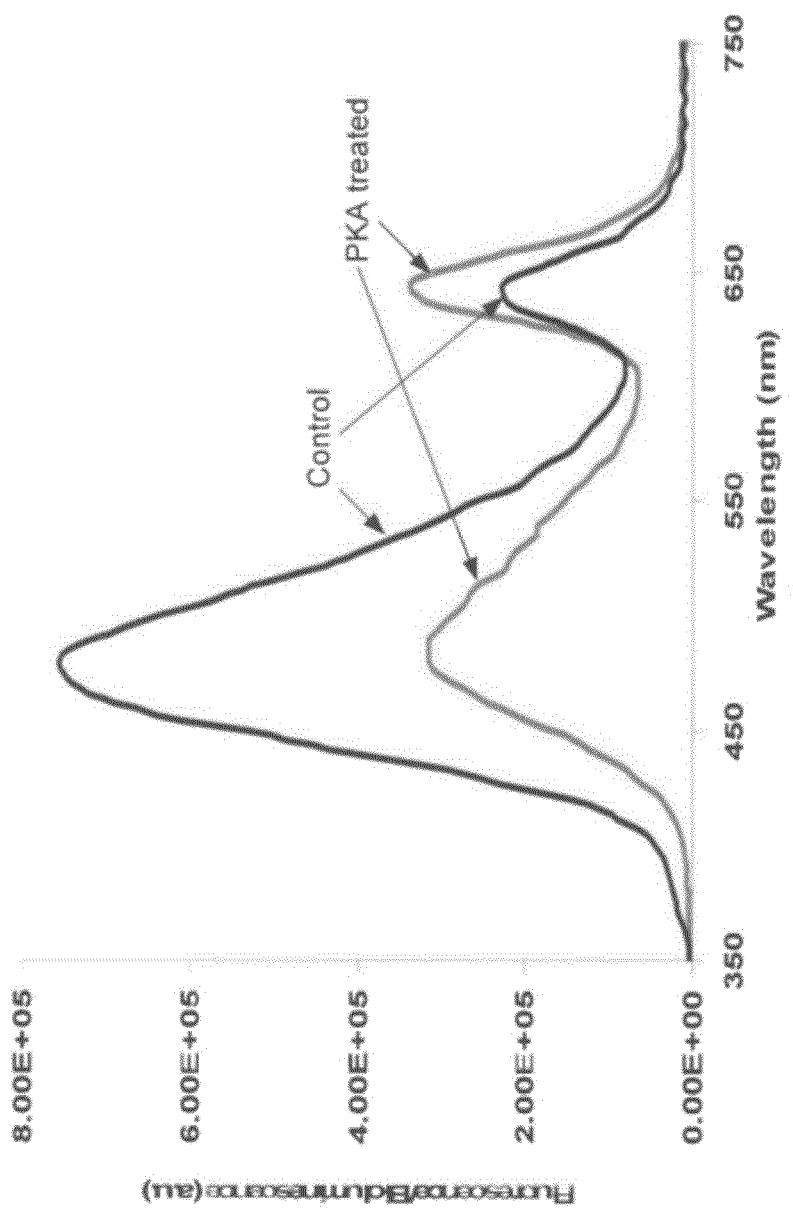
FIG. 22 illustrates the detection of the PKA by QD BRET sensor.

Protein kinase is a family of more than 500 enzymes that facilitate the transfer of the γ-phosphoryl group of ATP to serine, threonine, and tyrosine residues during protein/peptide phosphorylation. Protein kinases are found to be critical in both normal physiological processes and variety of diseases including cancer. This example establishes a platform for a multiplexed high throughput protein kinase activity assay by using quantum dots and bioluminescence proteins. This QD BRET assay, in contrast to the commonly used fluorescence-based methods, has the advantage of low background and no need for external illumination. To establish the assay platform, the Protein Kinase A (PKA) has been selected as the model target for the system development. FIG. 21 illustrates an embodiment of such an assay. In particular, FIG. 21 illustrates a schematic of the PKA detection based on the formation of the self-illuminating complex mediated by the PKA phosphorylation. The substrate of PKA, kemptide is a short peptide, and can be conjugated to quantum dots (FIG. 21a) or to the bioluminescent protein such as Luc8 (FIG. 21b). The conjugated kemptide will be phosphorylated in the presence of ATP by PKA. Phosphorylated kemptides can be detected by a physpho-specific antibody or metal chelators (such as GaIII) conjugated to a bioluminescent protein (FIG. 21a) or to quantum dots (FIG. 21b). This coupling event brings quantum dots and the bioluminescence protein to close proximity so as to allow bioluminescence resonance energy transfer (BRET) to occur upon the addition of a substrate. FIG. 22 illustrates the result of the PKA detection by the method FIG. 21b. The BRET ratio was increased from 0.15 to 0.47 after the PKA phosphorylation of the substrate kemptide.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and protected by the following claims.

```
                                               SEQ ID NO: 1
(Rluc)
MTSKVYDPEQ RKRMITGPQW WARCKQMNVL DSFINYYDSE

KHAENAVIFL HGNAASSYLW RHVVPHIEPV ARCIIPDLIG

MGKSGKSGNG SYRLLDHYKY LTAWFELLNL PKKIIFVGHD

WGACLAFHYS YEHQDKIKAI VHAESVVDVI ESWDEWPDIE

EDIALIKSEE GEKMVLENNF FVETMLPSKI MRKLEPEEFA

AYLEPFKEKG EVRRPTLSWP REIPLVKGGK PDVVQIVRNY

NAYLRASDDL PKMFIESDPG FFSNAIVEGA KKFPNTEFVK

VKGLHFSQED APDEMGKYIK SFVERVLKNE Q

SEQ ID NO: 2
(Rluc8)
MASKVYDPEQ RKRMITGPQW WARCKQMNVL DSFINYYDSE

KHAENAVIFL HGNATSSYLW RHVVPHIEPV ARCIIPDLIG

MGKSGKSGNG SYRLLDHYKY LTAWFELLNL PKKIIFVGHD

WGAALAFHYA YEHQDRIKAI VHMESVVDVI ESWDEWPDIE

EDIALIKSEE GEKMVLENNF FVETVLPSKI MRKLEPEEFA

AYLEPFKEKG EVRRPTLSWP REIPLVKGGK PDVVQIVRNY

NAYLRASDDL PKLFIESDPG FFSNAIVEGA KKFPNTEFVK

VKGLHFLQED APDEMGKYIK SFVERVLKNE Q
```

We claim the following:

1. A conjugate system, comprising: a self-illuminating quantum dot conjugate and a bioluminescence initiating compound, wherein the self-illuminating quantum dot conjugate includes a bioluminescence donor molecule and a quantum dot, wherein the bioluminescence donor molecule is directly bound to the quantum dot, wherein the bioluminescence donor molecule and the bioluminescence initiating compound interact to produce a bioluminescence energy, and wherein the quantum dot emits a fluorescence energy in response to the non-radiative transfer of the bioluminescence energy from the bioluminescence donor molecule to the quantum dot.

2. The system of claim 1, wherein the bioluminescence donor molecule is a Luciferase protein.

3. The system of claim 1, wherein the bioluminescence donor molecule is a *Renilla* Luciferase protein.

4. The system of claim 1, wherein the bioluminescence donor molecule is a mutated *Renilla* Luciferase protein comprising SEQ ID NO: 2.

5. The system of claim 1, wherein the self-illuminating quantum dot conjugate includes a first agent.

6. The system of claim 5, wherein the first agent has an affinity for a target, where the target is selected from the group consisting of: a compound, a polypeptide, a polynucleotide, an antibody, an antigen, a hapten, a cell type, a tissue type functional group and a tissue type.

7. The system of claim 5, wherein the self-illuminating quantum dot conjugate includes a second agent, wherein the second agent is effective at treating a disease.

8. The system of claim 1, wherein the self-illuminating quantum dot conjugate includes a second agent, wherein the second agent is effective at treating a disease.

9. The system of claim 1, wherein the quantum dot comprises a core and a cap.

10. The system of claim 9, wherein the core of the quantum dot is selected from the group consisting of: IIB-VIB semiconductors, IIIB-VB semiconductors, and IVB-IVB semiconductors; and wherein the cap is selected from: IIB-VIB semiconductors of high band gap.

11. The structure of claim 10, wherein the core of the quantum dot is selected from the group consisting of: CdS and CdSe, and the cap is selected from ZnS and CdS.

12. The system of claim 11, wherein the bioluminescence donor molecule is a Luciferase protein.

13. The system of claim 12, wherein the bioluminescence donor molecule is a mutated *Renilla* Luciferase protein comprising SEQ ID NO: 2.

14. The system of claim 13, wherein the quantum dot is CdSe/ZnS.

15. The system of claim 1, wherein the bioluminescence initiating compound is selected from the group consisting of: coelenterazine, analogs, and functional derivatives thereof, and D-luciferin analogs, and functional derivatives thereof.

16. The conjugate system of claim 1, wherein the quantum dot comprises a quantum dot composite.

17. The system of claim 6, wherein the self-illuminating quantum dot conjugate includes a second agent, wherein the second agent is biocompatibility agent.

* * * * *

SEQUENCE LISTING

<160> NUMBER OF SEQ ID NOS: 2

<210> SEQ ID NO 1
<211> LENGTH: 311
<212> TYPE: PRT
<213> ORGANISM: Renilla Luciferase

<400> SEQUENCE: 1

Met Thr Ser Lys Val Tyr Asp Pro Glu Gln Arg Lys Arg Met Ile Thr

```
              1               5                  10                 15
Gly Pro Gln Trp Trp Ala Arg Cys Lys Gln Met Asn Val Leu Asp Ser
             20                  25                 30

Phe Ile Asn Tyr Tyr Asp Ser Glu Lys His Ala Glu Asn Ala Val Ile
             35                  40                 45

Phe Leu His Gly Asn Ala Ala Ser Ser Tyr Leu Trp Arg His Val Val
 50                  55                 60

Pro His Ile Glu Pro Val Ala Arg Cys Ile Ile Pro Asp Leu Ile Gly
 65                  70                 75                 80

Met Gly Lys Ser Gly Lys Ser Gly Asn Gly Ser Tyr Arg Leu Leu Asp
                 85                 90                 95

His Tyr Lys Tyr Leu Thr Ala Trp Phe Glu Leu Leu Asn Leu Pro Lys
                100                105                110

Lys Ile Ile Phe Val Gly His Asp Trp Gly Ala Cys Leu Ala Phe His
                115                120                125

Tyr Ser Tyr Glu His Gln Asp Lys Ile Lys Ala Ile Val His Ala Glu
            130                135                140

Ser Val Val Asp Val Ile Glu Ser Trp Asp Glu Trp Pro Asp Ile Glu
145                150                155                160

Glu Asp Ile Ala Leu Ile Lys Ser Glu Glu Gly Glu Lys Met Val Leu
                165                170                175

Glu Asn Asn Phe Phe Val Glu Thr Met Leu Pro Ser Lys Ile Met Arg
                180                185                190

Lys Leu Glu Pro Glu Glu Phe Ala Ala Tyr Leu Glu Pro Phe Lys Glu
            195                200                205

Lys Gly Glu Val Arg Arg Pro Thr Leu Ser Trp Pro Arg Glu Ile Pro
        210                215                220

Leu Val Lys Gly Gly Lys Pro Asp Val Val Gln Ile Val Arg Asn Tyr
225                230                235                240

Asn Ala Tyr Leu Arg Ala Ser Asp Asp Leu Pro Lys Met Phe Ile Glu
                245                250                255

Ser Asp Pro Gly Phe Phe Ser Asn Ala Ile Val Glu Gly Ala Lys Lys
            260                265                270

Phe Pro Asn Thr Glu Phe Val Lys Val Lys Gly Leu His Phe Ser Gln
        275                280                285

Glu Asp Ala Pro Asp Glu Met Gly Lys Tyr Ile Lys Ser Phe Val Glu
        290                295                300

Arg Val Leu Lys Asn Glu Gln
305                310

<210> SEQ ID NO 2
<211> LENGTH: 311
<212> TYPE: PRT
<213> ORGANISM: Renilla Luciferase

<400> SEQUENCE: 2

Met Ala Ser Lys Val Tyr Asp Pro Glu Gln Arg Lys Arg Met Ile Thr
1               5                  10                 15

Gly Pro Gln Trp Trp Ala Arg Cys Lys Gln Met Asn Val Leu Asp Ser
             20                  25                 30

Phe Ile Asn Tyr Tyr Asp Ser Glu Lys His Ala Glu Asn Ala Val Ile
             35                  40                 45

Phe Leu His Gly Asn Ala Thr Ser Ser Tyr Leu Trp Arg His Val Val
 50                  55                 60

Pro His Ile Glu Pro Val Ala Arg Cys Ile Ile Pro Asp Leu Ile Gly
```

```
                    65                  70                  75                  80
Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
                100                 105                 110

Lys Ile Ile Phe Val Gly His Asp Trp Gly Ala Ala Leu Ala Phe His
                115                 120                 125

Tyr Ala Tyr Glu His Gln Asp Arg Ile Lys Ala Ile Val His Met Glu
                130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
                180                 185                 190

Lys Leu Glu Pro Glu Glu Phe Ala Ala Tyr Leu Glu Pro Phe Lys Glu
                195                 200                 205

Lys Gly Glu Val Arg Arg Pro Thr Leu Ser Trp Pro Arg Glu Ile Pro
                210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
                260                 265                 270

Phe Pro Asn Thr Glu Phe Val Lys Val Lys Gly Leu His Phe Leu Gln
                275                 280                 285

Glu Asp Ala Pro Asp Glu Met Gly Lys Tyr Ile Lys Ser Phe Val Glu
                290                 295                 300

Arg Val Leu Lys Asn Glu Gln
305                 310
```